US005569830A

United States Patent [19]
Bennett et al.

[11] Patent Number: 5,569,830
[45] Date of Patent: Oct. 29, 1996

[54] PLANT INHIBITORS OF FUNGAL POLYGALACTURONASES AND THEIR USE TO CONTROL FUNGAL DISEASE

[75] Inventors: Alan Bennett; John M. Labavitch; Ann Powell, all of Davis; Henrik Stotz, Menlo Park, all of Calif.

[73] Assignee: Regents of the University of California, Oakland, Calif.

[21] Appl. No.: 238,163

[22] Filed: May 3, 1994

[51] Int. Cl.[6] .............................. A01H 1/04; C12N 5/14; C12N 15/00; C07H 17/00
[52] U.S. Cl. .................. 800/205; 536/23.6; 435/69.1; 435/172.3; 435/240.4; 424/93.21; 514/2
[58] Field of Search .................. 800/205, DIG. 44, 800/64; 536/23.6; 435/69.1, 172.3, 240.4; 424/93.2, 93.21; 514/2

[56] References Cited

U.S. PATENT DOCUMENTS 4,940,840  7/1990  Suslow et al. ..................... 800/205

OTHER PUBLICATIONS

Abu–Goukh, A. A., et al. (1983) "Purification and partial characterization of Bartlett pear fruit polygalacturonase inhibitors", *Physiological Plant Pathology,* 23:111–122.

De Lorenzo, Giulia, et al. (1990) "Host–pathogen interactions. XXXVII. Abilities of the Polygalacturonase–inhibiting proteins from four cultivars of *Phaseolus vulgaris* to inhibit the endopolygalacturonases from three races of *Colletotrichum lindemuthianum*", *Physiological and Molecular Plant Pathology,* 36:421–435.

Toubart, Patrick, et al. (1992) "Cloning and characterization of the gene encoding the endopolygalacturonase–inhibiting protein (PGIP) of *Phaseolus vulgaris* L.", *The Plant Journal,* 2:367–373.

Stotz, Henrik U., et al. (1993), "Molecular Characterization of a Polygalacturonase Inhibitor from *Pyrus communis* L. cv Bartlett", *Plant Physiol.,* 102:133–138.

*Primary Examiner*—David T. Fox
*Assistant Examiner*—Elizabeth F. McElwain
*Attorney, Agent, or Firm*—Townsend and Townsend and Crew LLP

[57]  ABSTRACT

The present invention provides isolated nucleic acid sequences encoding plant polygalacturonase inhibitor proteins (PGIP) which inhibit the activity of fungal polygalacturonases. Transgenic plants expressing a heterologous PGIP show increased resistance to fungi which normally infect the plants.

26 Claims, 11 Drawing Sheets

FIG. 1A.

```
ACATCTCTCAGGCTCTCTCAACCAAAACAATGGAACTCAAGTTCTCCACCTTCCTC      60
                          M  E  L  K  F  S  T  F  L
TCCCTAACCCTACTCTTCTCCGTCCTTAACCCCGCTCTCTCGATCTGCAACCCC        120
 S  L  T  L  F  S  V  L  N  P  A  L  S  D  L  C  N  P
                                           *
GACGACAAAAAAGTCCTCCTACAAATCAAGAAAGCCTTCGGGGACCCCTAGTCTTGGCC   180
 D  D  K  K  V  L  L  Q  I  K  K  A  F  G  D  P  Y  V  L  A
TCATGGAAATCAGACACTGACTGCTGCGATTGGTACTGCGTCACCTGTGACTCCACCACA 240
 S  W  K  S  D  T  D  C  C  D  W  Y  C  V  T  C  D  S  T  T
AACCGGCATTAACTCCCTCACCATCTTTGCCGGCCAGGTGTCAGGCCAAATCCCGCCCTA 300
 N  R  I  N  S  L  T  I  F  A  G  Q  V  S  G  Q  I  P  A  L
GTAGGAGACTTGCCATACCTTGAAACCCTTGAATTCCATAAGCAACCCAATCTCACTGGC 360
 V  G  D  L  P  Y  L  E  T  L  E  F  H  K  Q  P  N  L  T  G
CCAATCCAACCCGCCATTGCCAAGCTCAAAGGACTCAAGTCTCTCAGGCTGAGCTGGACC 420
 P  I  Q  P  A  I  A  K  L  K  G  L  K  S  L  R  L  S  W  T
AACCTCTCAGGCTCTGTCCCTGACTTCCTCAGCCAACTCACAAGAACCTCACATTCCTGAC 480
 N  L  S  G  S  V  P  D  F  L  S  Q  L  K  N  L  T  F  L  D
CTCTCCTTCAACAACCTCACCGGTGCCATCCCCAGCTCGCTTTCTGAGCTCCCAAACCTC 540
 L  S  F  N  N  L  T  G  A  I  P  S  S  L  S  E  L  P  N  L
```

FIG. 1B.

```
GGCGCTCTTCGTCTAGACCGCAATAAGCTCACAGGTCATATTCCGATATCGTTTGGGCAG    600
 G  A  L  L  D  R  N  K  L  T  G  H  I  P  I  S  F  G  Q
TTCATTGGCAACGTTCCAGACCTGTATCTCTCCACAACCAGCTTTCTGGTAACATTCCA    660
 F  I  G  N  V  P  D  L  Y  L  S  H  N  Q  L  S  G  N  I  P
ACCTCATTCGCTCAGATGGACTTCACCAGCATAGACTTATCACGGAACAAGCTGAAGGT    720
 T  S  F  A  Q  M  D  F  T  S  I  D  L  S  R  N  K  L  E  G
GACGCATCCGTGATATTTGGGCTGAACAAGACAACCCAGATTGTGGACCTGTCCAGGAAC    780
 D  A  S  V  I  F  G  L  N  K  T  T  Q  I  V  D  L  S  R  N
     *                *
TTGCTGGAATTTAATCTGTCAAAGGTGGAGTTTCCGACAAGCTTGACCTCGCTGGATATC    840
 L  L  E  F  N  L  S  K  V  E  F  P  T  S  L  T  S  L  D  I
AACCACAATAAGATCTACGGGAGTATCCCAGTGGAGTTTACGCAACTGAATTTCCAGTTC    900
 N  N  K  I  Y  G  S  I  P  V  E  F  T  Q  L  N  F  Q  F
CTGAACGTGAGCTACAACAGGCTGTGTGGTCAGATTCCTGTGGGTGGAAAGTTGCAGAGC    960
 L  N  V  S  Y  N  R  L  C  G  Q  I  P  V  G  G  K  L  Q  S
TTCGACGAGTATTCTTATTTCCATAACCGATGCTTGTGCGGTGCTCCACTCCCAAGCTGC    1020
 F  D  E  Y  S  Y  F  H  N  R  C  L  C  G  A  P  L  P  S  C
AAGTAAAAGGCCACAACTGCAGATTTGGCCAGCAATTT
 K
```

FIG. 2A.

```
ttagacaaactttaccccaggaaggtgtcatcttaaatcaatcaaaatat
atattttcatcctaaactcacttactttaaaaagaatctattcttactt
aaacacttaacattttaaaaacatttttcatttttagtatcctttattt
ataatcaatttaattaaatatctatgataaaacatcatgattaataa
attgtaaaatcattggacatctctttgagtttgaattcaaagccaa
cgcattatattcttagatactgatacacaccatgtgactagtgactgtg
gggcagttttctttgaccaaaaatccgtattgctaaaatatgacccttt
ttttgtttttataaataccaatgagctaagttatataataatattgttcat
aaacaaaaaaaaaaaaaaatATGAACTTGTCTCTTCTTTCTTGTAGTTATT     10
                    M   N   L   S   L   L   L   V   V   I
TTTCTTTGCTTTCTGCTTCTCCTTCACTATCAGTAAGATGCAATCCGAAAGA     27
F   L   C   F   A   S   P   S   L   S   V   R   C   N   P   K   D
CAAAAAAGTCCTTCTACAAATAAAGAAAGACTTAGGCAATCCTTACCATT       43
    K   K   V   L   L   Q   I   K   K   D   L   G   N   P   Y   H
TAGCTTCATGGGATCCAAACACAGATTGCTGTTACTGGTACGTCATAAAA       60
L   A   S   W   D   P   N   T   D   C   C   Y   W   Y   V   I   K
TGTGACCGGAAAACCAACCGGATAAATGCTCTTCACCGTCTTCCAAGCCAA      77
    C   D   R   K   T   N   R   I   N   A   L   T   V   F   Q   A   N
TATCTCCGGCCAAATTCCGGCAGCCGTCGGAGACCTTCCATATCTCGAAA
```

FIG. 2B.

```
I  S  G  Q  I  P  A  A  V  G  D  L  P  Y  L  E                          93
CATTGGAATTTCATCATGTTACTAATCTTCACCGGAACAATTCCACCTGCA

T  L  E  F  H  H  V  T  N  L  T  G  T  I  P  P  A                      110
ATTGCGAAGCTCACAAATCTCAAAATGTTAAGGCTTCAGCTTCACTAACCT

I  A  K  L  T  N  L  K  M  L  R  L  S  F  T  N  L                      127
TACAGGTCCGATCCCTGAATTCCTTAGTCAGCTGAAGAATTTGACGTTGC

T  G  P  I  P  E  F  L  S  Q  L  K  N  L  T  L                         143
TCGAGTTGAATTACAATCAATTACCGGAACAATCCCTTCTCCCTCTCT

L  E  L  N  Y  N  Q  F  T  G  T  I  P  S  S  L  S                      160
CAGCTTCCGAATTGCTAGCGATGTACTTAGATCGTAACAAACTCACCGG

Q  L  P  N  L  L  A  M  Y  L  D  R  N  K  L  T  G                      177
AACAATACCGGAATCGTTTGGGAGATTTAAAGGACCAAATATACCAGATC

T  I  P  E  S  F  G  R  F  K  G  P  N  I  P  D                         193
TCTACCTTTCACACAAGCTTGACCGGACATGTGCCGGCATCTTTAGGT

L  Y  L  S  H  N  S  L  T  G  H  V  P  A  S  L  G                      210
GATTTGAATTTTTCCACGCTTGATTTCTCCAGGAATAAGCTTGAAGGAGA

D  L  N  F  S  T  L  D  F  S  R  N  K  L  E  G  D                      227
TGTTTCGTTTTTGTTCGGGAAGAATAAGACGAGTCAGGTAATTGATTTAT
```

FIG. 2C.

```
V  S  F  L  F  G  K  N  K  T  S  Q  V  I  D  L                              243
CGAGGAATTTATTGGAGTTTGATATTTCGAAATCGGAGTTTGCTGAGAGC
 S  R  N  L  L  E  F  D  I  S  K  S  E  F  A  E  S                          260
TTGATATCATTGGATTTGAATCATAATCGAATTTTTGGTAGCTTACCACC
 L  I  S  L  D  L  N  H  N  R  I  F  G  S  L  P  P                          277
AGGATTGAAAGATGTACCATTGCAGTTTTTCAATGTGAGTTATAATAGAC
 G  L  K  D  V  P  L  Q  E  F  N  V  S  Y  N  R                             293
TTTGTGGACAGATTCCACAAGGTGGAACGTTGCAGAGCTTTGATATTTAC
 L  C  G  Q  I  P  Q  G  G  T  L  Q  S  F  D  I  Y                          310
TCTTATTTGCATAACAAATGCCTTTGTGGCTCTCCCCTTGCCGAAATGTAA
 S  Y  L  H  N  K  C  L  C  G  S  P  L  P  K  C  K                          327
GTAGgtatgggggtcgaggattaaatcgagaattgtagtagaggca
    *
actagccttctctagtcgtcgttcctaatcatatttagtgctctttggcttt
ttataattcgtatgcgagggtctaatgaatagtctctctatcaataaa
ctggcatctcagatcttccagttatgaaatttacgaagtatgttgttgat
caatattactgccctgattcatgtcttcatcttttttttctcttttctc
aagttgcaatatttgaaagcaaattgaattgggcatgtagttacaaactt
tgaagttagttagtcaatttgaatcttgcaatagtcaaatgagctaaagt
caaaagtgtattaaaaatttataaacaagtgcatataaacagagttga
accaaaggctaatagatggtgcaaattgaggtgcatttcattatgggtcgt
```

FIG. 2D.

```
gttttgtttcattggaggagttcacaacgcaaagtccgtgtgctaaagt
tactgaattttcaatagaagtacagaatctgtgtctaaaattatttacag
aatctgtgctaaaattattgagtcatacactgtggaacagttgcaagatt
agatgaaggaattgttacttcattgagaaattatttcacaacttacat
taatctttatcgatgttaataaact
```

Figure 3

```
Tomato  MN-----LS----LLLVVIFLCFASPSLSVRCNPKDKKVLLQIKKDLGNP          41
Pear    ME-----LKFSTFLSLTLLFSSVLNPALSDLCNPDDKKVLLQIKKAFGDP          45
Bean    MTQFNIPVTMSSSLSIILVILVSLRTALSELCNPQDKQALLQIKKDLGNP          50
        *.           *      **   ***.. *.. *******..*.*.

Tomato  YHLASWDPNTDCCY--WYVIKCDRKTN--RINALTVFQANISGQ--IPAA         85
Pear    YVLASWKSDTDCCD--WYCVTCDSTTN--RINSLTIFAGQVSGQ--IPAL         89
Bean    TTLSSWLPTTDCCNRTWLGVLCDTDTQTYRVNNLDLSGHNLPKPYPIPSS        100
        *.**..**   *** .*   * *.* *   . *   .     *.  . *

Tomato  VGDLPYLETLEFHHVTNLTGTIPSSLSQLPNLLAMYLDRNKLTGTIPEFL         135
Pear    VGDLPYLETLEFHKQPNLTGPIQPAIAKLKGLKSLRLSWTNLSGSVPDFL         139
Bean    LANLPYLNFLYIGGINNLVGPIPPAIAKLTQLHYLYITHTNVSGAIPDFL         150
         ..***  .*      **  *  . .* .*.    *     * * *.**

Tomato  SQLKNLTLLELNYNQFTGTIPSSLSQLPNLLAMYLDRNKLTGTIPESFGR         185
Pear    SQLKNLTFLDLSFNNLTGAIPSSLSELPNLGALRLDRNKLTGHIPISFGQ         189
Bean    SQIKTLVTLDFSYNALSGTLPPSISSLPNLGGITFDGNRISGAIPDSYGS         200
        **.* *  *     .   .  . *. **  . .  ..* ..* ** . .

Tomato  FKGPNIPDLYLSHNSLTGHVPASLGDLNFSTLDFSRNKLEGDVSFLFGKN         235
Pear    FIG-NVPDLYLSHNQLSGNIPTSFAQMDFTSIDLSRNKLEGDASVIFGLN         238
Bean    F-SKLFTAMTISRNRLTGKIPPTFANLNLAFVDLSRNMLEGDASVLFGSD         249
        *     .  .*..  .   . .  .  .  . .***. .***.*..**
```

```
PGIP                   P--   L    L    -L-L3-N-L-G-I
RKLS                   P--L--L--L--L--L--N-LSG-I
Adenylate Cyclase      P--L--L--L--L--L--N  L  L
GP1bα                  P-GLL--LP-L--L-LS-N-LTTL
L rich α2GP            P--LL----L--L--L--N-L--L
C-peptidase N          P--LF--L--L--L--L--N-L--L
Toll                   P--LF-H--NL--L--L--N-L--L
Chaoptin               P---F--L---LDLS-N-L--I
odo22+                 --L--L--L--L--L--N--L---l
```

PLANT INHIBITORS OF FUNGAL POLYGALACTURONASES AND THEIR USE TO CONTROL FUNGAL DISEASE

This invention was made with Government support under Grant No. DCB 8916127 awarded by the National Science Foundation, Grant No. 9300835 awarded by the U.S. Department of Agriculture and Grant No. LAB-78-83-C awarded by the California Tomato Board. The Government has certain rights in this invention.

BACKGROUND OF THE INVENTION

The present invention relates to nucleic acids encoding inhibitors of fungal polygalacturonases. The nucleic acids are used to produce fungus-resistant transgenic plants.

Control of fungal plant pathogens is of major economic importance. For instance, extensive efforts have been focussed on controlling fungal rot in fruits. Previous research has involved hygienic and chemical means to control the fungi (Raese, *Hort. Rev* 11:357 (1989) and Pimentel et al., *BioScience* 42:750 (1992)). Some reduction in fruit rotting has been achieved by careful handling of picked fruit, by hygienic washing, by reducing the storage temperature of the ripening fruit, breeding fungus-resistant cultivars and by the application of effective fungicides. Little success has been achieved by breeding programs to select for fruit that are more resistant to fungi such as *Botrytis cinerea, Glonierella citigulata,* and *Alternaria alterizata.*

Recently, research has focused on the plant's response to attack by fungi, centering on induced enzymatic activities such as chitinases, which can attack fungi directly (Meins & Ahl, *Plant Science* 61:155 (1989)). Infection by the fungal pathogen, *Cercospora nicotianae*, was partially reduced in tobacco plants expressing large amounts of tobacco chitinase gene (Neuhaus et al., *Plant Mol. Biol.* 16:141 (1991)). In addition, other genes for enzymes in induced plant defense pathways, such as phytoalexin biosynthesis, have been introduced into transgenic tobacco plants and have been shown to partially retard the invasion by the fungal pathogen, *B. cinerea* (Hain et al., *Nature* 361:153 (1993)).

Fungal pathogens invade plant tissues by the secretion of enzymes which degrade components of the plant cell wall. A major class of enzyme secreted by fungal plant pathogens are polygalacturonases which degrade pectic cell wall components. One of the ways in which plants combat fungal infection is by the production of polygalacturonase inhibitor proteins (PGIPs) (Albersheim & Anderson, *Physiol. Plant Path.* 2:339 (1972); Fielding, *Gen. Micro.* 123:377 (1981); Abu-Goukh et al., *Physiol Plant Path.* 23:111 (1983); Hahn et al., in T. Kosuge & E. Nester, *Plant Microbe Interactions*, Vol. 3, (1989)).

The nucleic acid sequence of a PGIP from *Phaseolus vulgaris* has been previously reported (Toubart et al., *Plant J.* 2:367, 1992). This PGIP is expressed at low levels throughout the bean plant and is a non-competitive inhibitor of polygalacturonase from *Colletotrichum lindemuthianum* (De Lorenzo et al., *Physiol. Mol. Plant Path.* 36:421 (1990)). PGIP from pears is a competitive inhibitor of polygalacturonase from *B. cinerea* (Abu-Goukh et al., *Physiol. Plant Path.* 23:111 (1983)) and is specifically expressed at high levels in the pear fruit.

Despite efforts to breed fungus-resistant plants, the prior art has yet to provide effective means of controlling a number of fungal infections in fruit. The present invention addresses these and other needs.

SUMMARY OF THE INVENTION

The present invention provides isolated DNA constructs comprising polynucleotide sequences encoding plant polygalacturonase inhibitor proteins (PGIPs). The sequences can be derived from pear or tomato. The polynucleotide sequences are preferably at least substantially identical to a sequence of least about 50 nucleotides from FIGS. 1 or 2.

The DNA constructs of the invention can be used for the expression of PGIP. In these embodiments, the constructs further comprise a promoter, typically a fruit-specific plant promoter, operably linked to the polynucleotide sequence.

The invention also provides transgenic plants comprising a recombinant expression cassette comprising a plant promoter operably linked to a polynucleotide sequence encoding a PGIP. The expression cassette preferably contains a heterologous promoter operably linked to a sequence encoding pear PGIP. The plant can be tomato or strawberry, which is resistant to *Botrytis cinerea* infection.

The invention further provides methods of conferring resistance to fungal infection in plants. The methods comprise introducing into plant tissue a recombinant expression cassette comprising a plant promoter operably linked to a polynucleotide sequence encoding a PGIP; regenerating the plant tissue into a whole plant, whereby the regenerated plant transcribes the polynucleotide sequence; and selecting plants which are resistant to fungal infection. The recombinant expression cassette can be introduced into the plant tissue using Agrobacterium or by a sexual cross.

Methods of isolating a PGIP gene from a plant are also provided. The methods comprise probing a DNA library (e.g., a cDNA library) prepared from the plant with oligonucleotide probes comprising a polynucleotide sequence from an isolated PGIP gene.

DEFINITIONS

A "heterologous sequence" is one that originates from a foreign species, or, if from the same species, is substantially modified from its original form. For example, a heterologous promoter operably linked to structural gene is from a species different from that from which the structural gene was derived, or, if from the same species, is substantially modified from its original form.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The phrase "polynucleotide sequence" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

A "polynucleotide encoding a PGIP" is a subsequence or full length polynucleotide sequence of a PGIP gene, such as the pear PGIP gene, which, when present in a transgenic plant has the desired effect, for example, inhibiting activity of fungal polygalacturonases. A full length polynucleotide sequence is one comprising substantially all (e.g., at least 95%) of the nucleotides in a cDNA or genomic DNA encoding a PGIP. Normally, fragments of the full-length sequence are between about 50 nucleotides and about 750 nucleotides, sequences consisting of about 100 nucleotides to about 500 nucleotides are more usual.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence encoding a PGIP". In addition, the term specifically includes those sequences substantially identical (determined as described below) with a PGIP gene sequence and that encode proteins that retain the function of the PGIP protein. Thus, in the case of pear PGIP gene disclosed here, the above term includes variant polynucleotide sequences which have substantial identity with the sequences disclosed here and which encode proteins capable of inhibiting the same fungal polygalacturonases as the native protein.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85:2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" as applied to polynucleotide sequences means that a polynucleotide comprises a sequence that has at least about 60% sequence identity, preferably at least about 80%, more preferably at least about 90% and most preferably at least about 95%, compared to a reference sequence using the programs described above (e.g., BESTFIT) using standard parameters.

As applied to polypeptides, the term "substantial identity" means that two peptide sequences, when optimally aligned, such as by the programs GAP or BESTFIT using default gap weights, share at least 80%, preferably at least 90%, more preferably at least 95% or more (e.g., 99%) of their sequences. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point Tm) for the specific sequence at a defined ionic strength and pH. The Tm is the temperature (under defined ionic strength and pH) at which 50% of the target sequence hybridizes to a perfectly matched probe. Typically, stringent conditions for a Southern blot protocol involve washing at 55° C with a 0.2XSSC wash.

As used herein, a homolog of a particular PGIP gene (e.g. the pear PGIP gene) is a second gene (either in the same plant type or in a different plant type) which encodes a polypeptide having at least 20 contiguous amino acid residues which are substantially identical or substantially similar (determined as described above) to a sequence in the protein encoded by the first gene. It is believed that, in general, homologs share a common evolutionary past.

The term "operably linked" refers to functional linkage between a promoter and a second sequence, wherein the promoter sequence initiates transcription of RNA corresponding to the second sequence.

The term "promoter" refers to a region of DNA upstream from the structural gene and involved in recognition and binding RNA polymerase and other proteins to initiate transcription. A "plant promoter" is a promoter capable of initiating transcription in plant cells.

The terms "resistant to fungal infection" and "fungus resistant" refer to transgenic plants of the invention which show increased ability to inhibit fungal infection as compared to the cultivar from which they are derived. Typically, this ability is measured in assays described below in which the formation of lesions is monitored after plant tissue is inoculated with the appropriate fungal spores. A "fungus resistant" plant of the invention is one in which infection is at least about 30% less than that of control plants, typically at least about 50% less, preferably less than about 70% as measured using these assays.

BRIEF DESCRIPTION OF THE DRAWINGS

FIG. 1 shows the nucleic acid (Seq. I.D. No.: 1) and amino acid (Seq. I.D. No.: 2) sequences of the pear PGIP cDNA obtained from mature green fruit. The site of potential signal peptide cleavage is indicated with a vertical arrow. The amino acid sequence identical to that determined for the purified pear PGIP is underlined and amino acids that were not possible to sequence in the protein are marked with an asterisk. The seven potential N-glycosylation sites (N-X-T/ S) are underlined twice.

FIG. 2 shows the genomic sequence (Seq. I.D. No.: 3) and predicted amino acid sequence (Seq. I.D. No.: 4) encoded by the PGIP gene from tomato. The DNA sequence of the open reading frame is shown in upper case. The stop codon is indicated by an asterisk. A polyadenylation site is underlined.

FIG. 3 is a comparison of the deduced amino acid sequences of PGIPs from tomato, pear and bean (Seq. I.D. No.: 5). The position of the N-terminus for each of the mature proteins is marked with an arrow. Identical amino acids are indicated by asterisks and conservative amino acid changes by a point. Potential N-glycosylation sites are shown in bold. Cysteine residues are underlined.

FIG. 6A shows alignment of leucine rich tandem repeats of tomato PGIP. conserved amino acids are shown in bold. The sequence was condensed or expanded at six different positions for an optimal alignment of the consensus sequence.

FIG. 6B is a comparison of consensus sequences of PGIP with other proteins with leucine rich repeats. The PGIP consensus was derived from the tomato, pear, and bean sequences with amino acids resent in a specific location in at least 50% of the repeats.

DETAILED DESCRIPTION OF INVENTION

Figure 4:
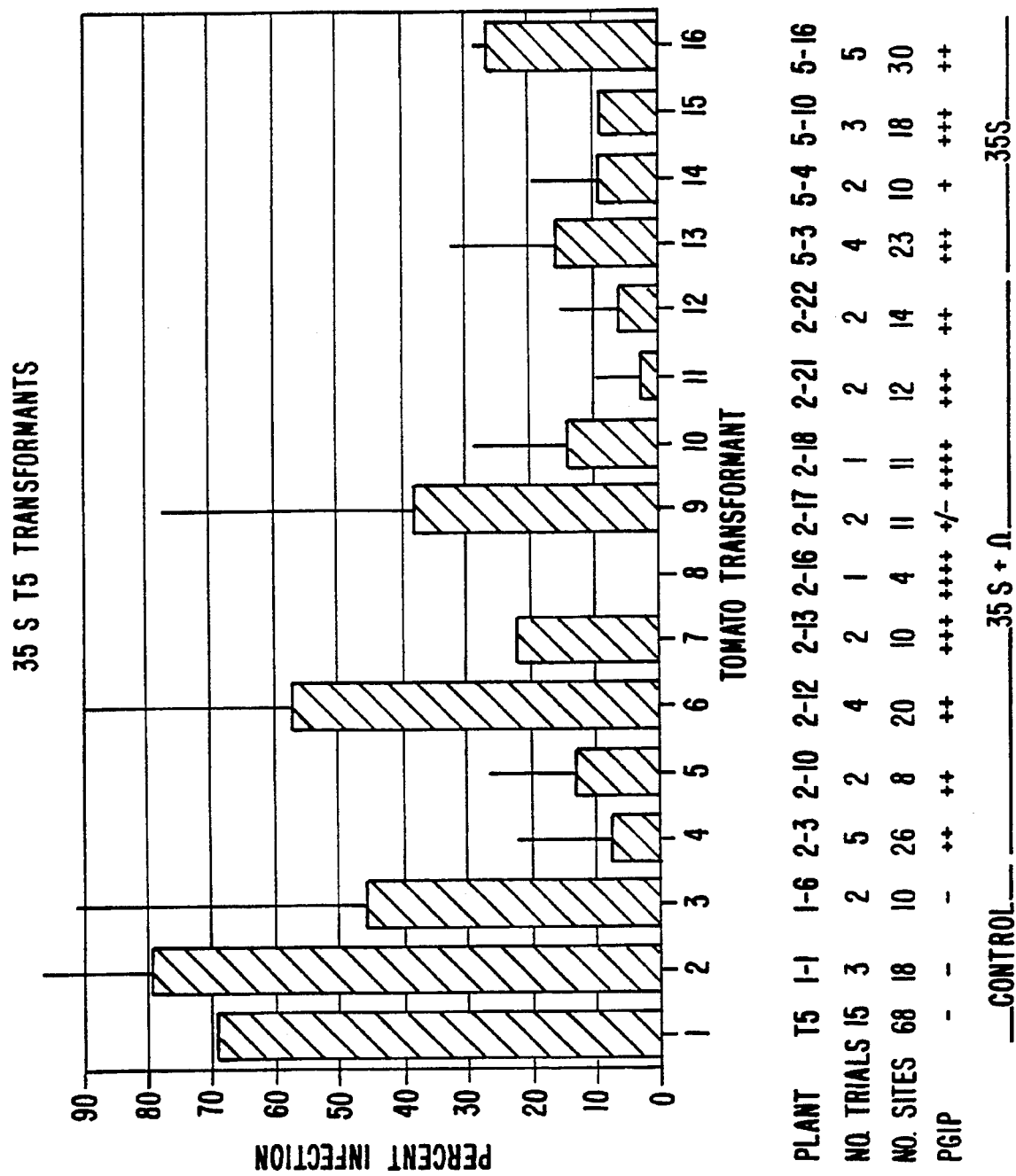
FIG. 4 shows percent of sites on each fully ripe tomato fruit forming sporulating lesions after inoculation of 1 mm depth wound sites with $10^3$ B. cinerea spores in 10 µl water. The data for the control fruit (T5, 1—1, 1–6) are expressed as percent of sites forming lesions. Data for the transgenic fruit are expressed as a percent of the infection from the controls.

This invention provides a genetic means to expand the resistance of fruit to rotting by fungi. This increased resistance allows longer storage of fruit, in less refrigerated conditions, and a reduction in the amount of fungicides applied to control decay, allowing for the marketing of fruits that have been exposed to fewer potentially carcinogenic chemicals.

Although protein inhibitors of fungal polygalacturonases have been identified in many tissues and may be ubiquitous, they appear to differ in their ability to inhibit polygalacturonases. Previous results indicate that the protein inhibitor of fungal polygalacturonases isolated from pear fruit differs in its efficacy against several pathogen polygalacturonases. For instance, comparison of pear and tomato polygalacturonase inhibitors indicates that the pear inhibitor is at least 10-fold more effective in inhibiting polygalacturonase from the fungal pathogen, Botrytis cinerea. Based on these data, it is clear that plant protein inhibitors of polygalacturonases differ in their efficacy. Thus, the differences in anti-fungal activity among PGIPs from various plants can be exploited to specifically target pathogens known to be significant problems for particular plant species.

The present invention provides cDNA sequences from pear fruit RNA that accurately encode pear PGIP (FIG. 1). Data provided here indicates that PGIP mRNA is abundant in pear fruit and flower structures but not in leaves, indicating organ specificity of its promoter. Since pear PGIP mRNA is abundant and only slightly induced upon fungal infection, it seems likely to be part of a preexisting defense system. Pear PGIP exhibits differential inhibition of polygalacturonases from different fungal species in agreement with the susceptibility of pears to these pathogens (Abu-Goukh et al., Physiol. Plant Path 23:101 (1983); Abu-Goukh & Labavitch, Physiol. Plant Path. 23:123 (1983)). Thus, introduction of the pear PGIP cDNA into other species alters the susceptibility of these species to the pathogens against which the pear PGIP is effective. For example, data presented herein indicates that transgenic tomato fruit expressing high levels of pear PGIP are more resistant to B. cinerea than control fruit.

The present invention also provides cDNA sequences encoding the tomato PGIP. This protein differs from pear PGIP in its efficacy as an inhibitor and may be directed against polygalacturonases from other groups of fungal plant pathogens. The expression of tomato PGIP in plant species, therefore, permits increased resistance to a group of pathogens different from that provided by pear PGIP.

The tomato PGIP was purified similarly from mature green tomato fruit. A fragment of tomato genomic DNA without introns was identified. The sequence accurately encodes the PGIP protein. The nucleotide sequence encoding tomato PGIP is presented in FIG. 2. A comparison was made between the sequences for pear, bean and tomato (FIG. 3). Each of the plant PGIP sequences is quite divergent from the others. The two most similar are pear and tomato PGIPs, having 68% amino acid sequence identity.

In order to direct transgenic expression of PGIP in various plants, a PGIP coding region is linked to promoters that direct high levels of expression. DNA containing these sequences is introduced into appropriate cells, and fruit bearing plants expressing the pear PGIP sequences are regenerated. A preferred method of practicing the invention includes the introduction of sequences for PGIP into a plant, such as tomato or strawberry, using Agrobacterium mediated transformation (Fillatti et al., in D. J. Nevins & R. A. Jones, Tomato Biotechnology, 199, 1987). The spectrum of resistance of the resultant transgenic plants, particularly their fruit, to fungal infection is a criterion by which transgenic plants are tested for efficacy of the introduced gene. After the initial transformation, the trait can be transferred to other varieties by traditional genetic crosses. The selected transgenic plant varieties are used by growers to produce a fruit crop that can withstand storage for longer times without fungal infection, and/or with reduced applications of fungicides.

Generally, the nomenclature used hereafter and the laboratory procedures in recombinant DNA technology described below are those well known and commonly employed in the art. Standard techniques are used for cloning, DNA and RNA isolation, amplification and purification. Enzymatic reactions involving DNA ligase, DNA polymerase, restriction endonucleases and the like generally are performed according to the manufacturer's specifications. These techniques and various other techniques are generally performed according to Sambrook et al., Molecu-

*lar Cloning—A Laboratory Manual*, Cold Spring Harbor Laboratory, Cold Spring Harbor, N.Y., (1989).

I. Isolation of nucleic acid sequences encoding PGIP

The isolation of PGIP genes may be accomplished by a number of techniques. For instance, oligonucleotide probes which selectively hybridize to PGIP genes can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as a fruit, and a cDNA library which contains the PGIP gene transcript is prepared from the mRNA. Alternatively, cDNA may be prepared from mRNA extracted from other tissue types (organs) in which PGIP genes or homologs are expressed such as seeds, flowers, leaves, stems, and roots.

The cDNA or genomic library can then be screened using a probe based upon the sequence of a cloned PGIP gene such as pear PGIP. Degenerate probes based on the amino acid sequence of a purified protein can also be used. Probes may be used to hybridize with genomic DNA or cDNA sequences to isolate homologous genes in the same or different plant species. The use of such hybridization techniques for identifying homologous genes is well known in the an and need not be described further.

Other methods for isolating desired genes, such as transposon tagging, can also be used. Transposon tagging involves introducing a transposon into the plant which leads to a mutation of the target gene and a detectable phenotypic change in the plant. Using a probe for the transposon, the mutant gene can then be isolated. Using the DNA adjacent to the transposon in the isolated mutant gene as a probe, the normal wild type allele of the target gene can be isolated. See, e.g., Haring, et al., *Plant Mol. Biol.* 16:449–469 (1991) and Walbot, *Ann. Rev. Plant Mol. Biol.* 43:49–82 (1992).

Alternatively, polynucleotides may be synthesized by well-known techniques as described in the technical literature. See, e.g., Carruthers et at., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

II. Expression of PGIP

The isolated sequences prepared as described herein are introduced into the appropriate plant for expression of the desired PGIP. The nucleic acid segment to be introduced generally will be substantially identical to at least a portion of a full length PGIP gene. The introduced sequence, although typically full length, may be a fragment which encodes a polypeptide capable of inhibiting fungal polygalacturonases.

A. Construction of expression vectors

The selection of expression vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press). In addition to the gene of interest, the vectors typically comprise additional attached sequences which confer resistance to degradation of the nucleic acid fragment, which assist in the process of genomic integration, or which provide a means to easily select for those cells or plants which are transformed. Such sequences are advantageous and greatly decrease the difficulty of selecting useable transformed plants.

The recombinant vectors of the present invention typically comprise an expression cassette designed for initiating transcription of the desired polynucleotide sequences in plants. Companion sequences, of bacterial origin, are also included to allow the vector to be cloned in a bacterial host. The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

For expression in plants, the recombinant expression cassette will contain, in addition to the desired polynucleotide sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the transcription start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Other sequences conferring tissue specificity, response to environmental signals, or maximum efficiency of transcription may also be found in the promoter region. Such sequences are often found within 400 bp of transcription start site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of promoters which direct transcription in plant cells is suitable. The promoter can be either constitutive or inducible.

Constitutive promoters are those whose operation is relatively independent of the developmental stage of the cell in which they are contained. An exemplary constitutive promoter is the 35S promoter from cauliflower mosaic virus promoter.

Regulated or inducible promoters are those whose expression is controlled either temporally with respect to the developmental stage of the cell, or spatially with respect to different parts or organs of the plant. Exemplary inducible promoters include those from genes encoding ribulose-1,5-hisphosphate carboxylase, the chlorophyll binding proteins or the glycine-rich root protein genes. Promoters which drive expression in fruit tissues are particularly preferred. An exemplary fruit-specific promoter is the promoter form the E8 gene (Deikman & Fischer, EMBO J. 7:3315 (1988)). The operation of a promoter may also vary depending on its location in the genome. Thus, an inducible promoter may become fully or partially constitutive in certain locations.

As noted above, the pear PGIP is expressed primarily in fruit tissue. Thus, PGIP genes of the invention can also be a source of fruit-specific promoters. The genes can be used with their endogenous promoter or heterologous constructs comprising a promoter from one gene can be operably linked to a second structural gene. Methods for isolation of promoter sequences are known. For instance, a genomic DNA library can be probed to identify clones bearing the PGIP gene of interest. The 5' portion of the clone can then be characterized to identify and isolate the promoter sequences.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419–434, 1982. Polyadenylation sequences include, but are not limited to the Agrobacterium octopine synthase signal (Gielen et al., *EMBO J.*, 3:835–846, 1984) or the nopaline synthase signal (Depicker et at., *Mol. and Appl. Genet*, 1:561–573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

B. Transformation of plant cells by in vitro techniques

The various DNA constructs described above may be introduced into the genome of the desired plant by a variety of conventional techniques. For a review of gene transfer methods for plant and cell cultures see, Potrykus *CIBA Found. Symp.* 154:198 (1990). For example, the DNA construct may be introduced directly into the genomic DNA of the plant cell using polyethylene glycol precipitation (Paszkowski et al. *Embo J.* 3:2717–2722 (1984)) electroporation and microinjection of plant cell protoplasts (Fromm et at. *Proc. Natl. Acad. Sci. USA* 82:5824 (1985)), or the DNA constructs can be introduced into plant tissue using ballistic methods, such as DNA particle bombardment (Klein et al. *Nature* 327:70–73 (1987)).

Various plant viral vectors can also be used. For instance, cauliflower mosaic virus (CaMV) may be used as a vector for introducing DNA into plant cells. (Hohn et al., 1982 "Molecular Biology of Plant Tumors," Academic Press, New York, pp.549–560; Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modifxed vital portion of the recombinant plasmid is then excised from the parent bacterial plasmid, and used to inoculate the plant cells or plants.

*Agrobacterium tumefaciens*-meditated transformation techniques are the most commonly used techniques for transferring genes into plants. These techniques are well described in the scientific literature. See, for example Horsch et at. *Science* 233:496–498 (1984), Fraley et al. *Proc. Natl. Acad. Sci. USA* 80:4803 (1983), and Hooykaas *Plant Mol. Biol.* 13:327–336 (1989).

All species which are a natural plant host for Agrobacterium are transformable in vitro. Most dicotyledonous species can be transformed by Agrobacterium. Monocotyledonous plants, and in particular, cereals, are not natural hosts to Agrobacterium. There is growing evidence now that certain monocots can be transformed by Agrobacterium. Using novel experimental approaches cereal species such as rye (de la Pena et al., *Nature* 325:274–276, 1987), corn (Rhodes et al., *Science* 240:204–207, 1988), and rice (Shimamoto et al., *Nature* 338:274–276, 1989) may now be transformed.

After selecting the transformed cells, one can confirm expression of the desired heterologous structural gene. Simple detection of mRNA encoded by the inserted DNA can be achieved by well known methods in the art, such as Northern blot hybridization. The inserted sequence can be identified using the polymerase chain reaction (PCR) and Southern blot hybridization, as well. See, e.g., Sambrook, supra.

C. Regeneration of whole plants

Transformed plant cells (e.g., protoplasts) which are derived by any of the above transformation techniques can be cultured to regenerate a whole plant which possesses the transformed genotype and thus the desired nematode resistant phenotype. Such regeneration techniques rely on manipulation of certain phytohormones in a tissue culture growth medium. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The invention can be used to alter fungus resistance in virtually any plant of interest. Suitable plants include fruit crops such as banana (Musa sp.), citrus (Citrus sp.), strawberry (Fragaria Sp.), raspberry (Rubus sp.), mango (Mangifera sp.), melon (Cucumis sp.), tomato (Lycopersicon sp.), grapes (Vitus, sp.), pear (Pyrus sp.), apple (Malus sp.) cucumber (Cucumis sp.), and apricot, peach, cherry, plum and prune (Prunus sp.); vegetable crops such as pea (Pisum sp.), bean (Vicia sp.), broccoli and related crucifers (Brassica sp.), spinach (spinacia sp.), onion (Allium sp.), celery (Apium sp.), carrot (Daucus sp.), asparagus (Asparagus sp.), and artichoke (Helianthus sp.); grains such as corn (Zea sp.), wheat (Triticum sp.), rye (Secale sp.), oats (Avena sp.) and rice (Oryza, sp.); additional ornamental crops such as tulip (Tulipa sp.), snapdragon (Antirrhinum sp.), Iris (Iris sp.), carnation (Dianthus, sp.), Chrysanthemum sp., Orchids (Cymbidium and Cattleya sp.), pelargonium; beverage crops such as coffee (Coffea sp.) and tea (Thea sp.); herb crops such as mint (Mentha sp.), thyme (Thymus sp.) and marjoram (origanum sp.).

Strawberry plants are particularly preferred in the methods of the invention. Suitable strawberry cultivars for use in the invention include Chandler, Selva, redcoat, and the like. A number of methods for the regeneration and transformation of strawberry plants have been reported. In strawberry, plant regeneration has been reported from leaf derived calli (see, e.g., Jones et al. *Plant. Cell Tiss. Cul.* 12:235–241 (1988); Liu and Sanford *HortScience* 23:383–396 (1988); and Nehra et al. *Plant Sci.* 66:119–126 (1990)). Direct shoot regeneration from leaf disks has also been reported (Nehra et al. *J. Amer. Soc. Hort. Sci.* 114:1014–1018 (1989)). Nehra et al. (*Plant Cell Rep.* 9:10–13 (1990)) report the transformation of strawberry (*Fragaria x anannassa*) cultivar Redcoat using Agrobacterium. Leaf explants were incubated with *A. tumefaciens* strain MP90 and plants were regenerated from callus using the methods as described in Nehra et al. (1990), supra). James et al. (*Plant Science* 69:79–94 (1990)) describe Agrobacterium mediated transformation using disarmed binary vectors based on those describe in Bevan *Nuc. Acids. Res.* 12:8711–8721 (1984).

EXAMPLES

The following examples are provided by way of illustration only and not by way of limitation. Those of skill will readily recognize a variety of noncritical parameters which could be changed or modified to yield essentially similar results.

Example 1

Molecular Characterization of a Polygalacturonase Inhibitor from *Pyrus communis* L. cv Bartlett The methods used to isolate the sequences disclosed here are as described in Stotz et al. *Plant Physiol.* 102:133 (1993).

A polygalacturonase inhibitor glycoprotein with an apparent molecular mass of 43 kD was purified from pear (*Pyrus communis* L. cv Bartlett) fruit. Chemical deglycosylation of this protein decreased the molecular mass to 34 kD. Gas chromatographic analysis suggests that N-linked glycosylation accounts for the majority of sugar moieties. Partial amino acid sequence analysis of the purified polygalacturonase inhibitor protein provided information used to amplify a corresponding cDNA by polymerase chain reactions. Multiple cloned products of these reactions were sequenced and the same open reading frame was identified in all of the products. It encodes a 36.5–2 kD polypeptide containing the amino acid sequences determined by protein sequencing and predicts a putative signal sequence of 24 amino acids and seven potential N-glycosylation sites. The expression of polygalacturonase inhibitor is regulated in a tissue-specific manner. Activity and mRNA level were much higher in fruit than in flowers or leaves.

Plant Material

Mature green pear (*Pyrus communis* L. cv Bartlett) fruits from orchard trees at the University of California, Davis, served as the source for the purification of PGIP. If not used immediately, fruits were stored either in air or under controlled atmosphere (2% $O_2$, 5% $CO_2$) at 0° C. There was no apparent effect of storage on recovered PGIP activity. Flowers and leaves from young pear trees were collected at Armstrong Field Station, University of California, Davis.

PGIP Purification

PGIP was purified according to Abu-Goukh et al. (*Physiol. Plant Path.* 23:111 (1983)) with modifications. Five kilograms of fruit flesh were homogenized in an equal volume of extraction buffer (1 m sodium acetate, pH 6, 1M NaCl, 1% [w/v] PVP-40, 0.2% [w/v] sodium bisulfite). The homogenate was stirred on ice for 1 hour and then centrifuged at 15,000 g for 20 minutes. The supernatant was stored at 4° C., and the pellet was resuspended in 1 volume of extraction buffer and stirred again for 1 hour at 4° C. After centrifugation (15,000 g, 20 minutes), the two supernatants were combined. The protein which precipitated between 50 and 100% saturated ammonium sulfate was collected, resuspended in 0.1M sodium acetate, pH 6, and extensively dialyzed at 4° C. against 10 mM sodium acetate, pH 6.

The dialyzed ammonium sulfate fraction was mixed with an equal volume of 0.2 m sodium acetate, pH 6, 2M NaCl, 2 mM $CaCl_2$, 2 mM $MgCl_2$, 2 mM $MnCl_2$ (2x0 Con A buffer) and applied to a column of Con A-Sepharose 4B. Chromatography was performed at 4° C. Protein bound by the column was eluted using 250 mM α-methyl mannoside in Con A buffer. The eluent was dialyzed against 50 mM sodium acetate, pH 4.5 (buffer A), and then concentrated by ultrafiltration using a pressure cell fitted with a PM-10 membrane (Amicon, Danvers, Mass.).

PGIP was further purified by cation-exchange FPLC (Pharmacia, Uppsala, Sweden) using a Mono S column run at a flow rate of 0.5 mL/min. The column was equilibrated with buffer A and eluted with a linear NaCl gradient (to a final concentration of 0.5M NaCl in buffer A). The fractions containing PGIP activity were pooled and the buffer of the active material changed to 50 mM sodium phosphate, pH 7 (buffer B) using a Centricon-10 microconcentrator. An equal volume of 3.4M ammonium sulfate in buffer B was added to the sample, which was then separated by hydrophobic interaction FPLC (Phenyl-Superose HR 5/5) at a flow rate of 0.5 mL/min. A linear, declining gradient was created by mixing buffer B with and without 1.7M ammonium sulfate. Active fractions were pooled and stored at −80° C. after freezing in liquid nitrogen.

Purification of PGIP resulted in an approximately 250-fold increase in PGIP specific activity as measured by the agarose diffusion assay. PGIP activity was bound by Con A, indicating the presence of glucosyl and/or mannosyl residues. Based on the yield of purified PGIP, it appears to be an abundant protein in fruit, representing about 0.4% of the protein in the initial salt extract. The purified glycoprotein has a molecular mass of 43 kD when analyzed by SDS-PAGE. TFMS treatment of purified pear PGIP decreased its molecular mass to 34 kD, indicating that carbohydrates contribute approximately 20% of the total mass of the mature protein.

PGIP Activity Assay

Inhibition of endo-PG activity from the culture filtrate (Egli, Master's Thesis, University of California, Davis (1987)) of *B. cinerea* DEL 11 (obtained from Richard M. Bostock, Department of Plant Pathology, University of California, Davis) was determined by an agarose diffusion assay (Taylor and Secor, *Phytopathology* 78:1101–1103 (1988)) in the presence of 6.5 nmol/min of PG and 0.01% sodium polypectate (Sigma). Alternatively, inhibition was determined by a reducing sugar assay (Gross *HortScience* 17:933–934 (1982)) using 0.65 μmol/min of PG and 0.05% sodium polypectate in a buffer containing 37.5 mM sodium acetate, pH 4.5, and 10 mM EDTA. One unit of PGIP activity was defined as the amount of inhibitor needed to reach 50% of complete inhibition of *B. cinerea* PG activity.

Carbohydrate Analysis

Dried, purified PGIP (600 μg) was dissolved in 2M TFA. The solution was saturated with helium before hydrolysis at 121° C. for 1 h. The monosaccharides generated during the TFA treatment were convened into alditol acetates (Blakeney, et al., *Carbohydr. Res.* 113:291–299 (1983)) and examined by GLC and GC-MS (Greve and Labavitch, *Plant Physiol.* 97:1456–14671 (1991)). The analysis was performed on duplicate samples. Most of the sugar residues (Man, GlcNAc, Glc, Fuc, Xyl) associated with pear PGIP are typical of those found in N-linked glycans of plant glycoproteins (Table 1) and the presence of Xyl and Fuc indicates that, in the case of pear PGIP, some of them are complex. The presence of high quantities of Man is in agreement with the binding of PGIP to Con A.

TABLE 1

Gas chromatographic analysis of the carbohydrate composition of PGIP from pear fruit

| Sugar | Amount (μg/mg protein)* |
|---|---|
| Man | 182 |
| Fuc | 27 |
| GlcNac | 24 |
| Xyl | 23 |
| Glc | 9 |
| Ara | 8 |

*Averages of duplicate samples are presented.

Protein Gel Electrophoresis

Native pear fruit PGIP and PGIP that had been chemically deglycosylated using TFMS according to Karp et al. (*Biol. Chem.* 257:7330–7335 (1982)) were separated by SDS-PAGE according to standard techniques. Polyacrylamide gels (10%) were stained with Coomassie blue.

Protein Assay and Sequencing

Protein was determined by the method of Bradford *Anal. Biochem.* 72:248–254 (1976) using a Bio-Rad protein assay kit and BSA as a standard. The purified PGIP and its CNBr fragments were sequenced. The CNBr peptide fragments were separated by SDS-PAGE according to Promega Probe-Design Technical Manual (1990). After electroblotting to ProBlott membrane (Applied Biosystems, Foster City, Calif.) and Coomassie staining of the peptide fragments, individual bands were cut out and subjected to automated Edman degradation according to standard techniques.

PGIP Gene Isolation

N-terminal (DLXNPDDKKVLLQIKKAFGDPYVLA, Seq. I.D. No.: 6) and internal amino acid sequences (DFTSIDLSRNKLEGDAXVIFGLXKTTQIVDL, Seq. I.D. No.: 7) were determined. Primer 1 (5'-GGAATTCAAYC-CNGAYGAYAARAARGT-3', Seq. I.D. No.: 8, 128-fold degeneracy), primer 2 (5'-GCTCTAGATCDATNGA-NGTRAARTCCAT-3', Seq. I.D. No.: 9, 192-fold degeneracy), and primer 3 (5'-GGAATTCCAR-ATHAARAARGCNTTYGG-3', Seq. I.D. No.: 10, 192-fold degeneracy) were synthesized (Applied Biosystems). (N indicates A, T, C, or G; Y indicates T or C; R indicates A or G; H indicates A, T, or C; D indicates A, T, or G.) cDNA was obtained by reverse transcription of 100 ng of poly(A)$^+$ RNA from immature pear fruits using an oligo(dT$_{17}$) primer (Sambrook et al., supra). One-fifth of the first strand cDNA reaction or 1 μg of genomic DNA was used as a template together with primers 1 and 2 in subsequent PCR. The reactions were carried out in a Perkin-Elmer Cetus (Norwalk, Conn.) DNA Thermal Cycler using Taq DNA polymerase (Perkin-Elmer Cetus) for 40 cycles (one cycle=1 minutes at 94° C., 2 minutes at 48° C., and 3.5 minutes at 65° C.) according to the manufacturer's instructions. The identity of the PCR product was verified by amplifying 150 pg of DNA of the first PCR in a second PCR utilizing primers 2 and 3. The reaction conditions were the same as described above, although 25 cycles were used. The resulting 569-bp PCR product was gel purified and ligated into pCR1000 (Invitrogen, San Diego, Calif.).

The 5' end of the PGIP transcript was obtained by RACE-PCR (Frohman et al., *Proc. Natl. Acad. Sci. USA* 85:8998–9002 (1988)). Oligo(dT$_{17}$) was used to reverse transcribe 5 μg of poly(A)$^+$ RNA. The DNA templates were G-tailed using terminal deoxynucleotidyl transferase. An adaptor primer (5'-TFGTCGACGGATCCTTC$_{17}$-3', Seq. I.D. No.: 11) was used together with a gene-specific primer 4 (5'-TAGACGAAGAGCGCCGA-3', Seq. I.D. No.: 12) in subsequent PCR. The reactions were carded out for 40 cycles (one cycle=45 seconds at 94° C., 25 seconds at 45° C., 3 minutes at 72° C.). One-fiftieth of the reaction was used in a second round of PCR with the same primers for 40 cycles under identical conditions. The products were cloned into pCR1000.

RACE-PCR was also employed to obtain the 3' end of the PGIP transcript. An adaptor primer (5'-GACTCGAGTCGA-CATCGAT$_{17}$-3', Seq. I.D. No.: 3), was used for first-strand cDNA synthesis. This primer, together with gene-specific primer 5 (5'-AGGACTCAAGTCTCTCAG-3', Seq. I.D. No.: 14), was used in 40 cycles of PCR one cycle=45 seconds at 94° C., 25 seconds at 50° C., 3 minutes at 72° C.). The products were cloned into pCR 1000.

The complete PGIP coding sequence was amplified by 30 cycles of PCR (one cycle=1 minutes at 94° C., 2 minutes at 58° C., 2 minutes at 72° C.) with gene-specific primers 6 (5'-ACATCTCTCAGGCTCTCAACC-3', Seq. I.D. NO.: 15) and 7 (5'-AAATIGCTGGCCAAATCTGCAG-3', Seq. I.D. No.: 16). A single 1059-bp PCR product was obtained and cloned using pCR1000. All cloned PCR products were sequenced in the pCR1000 vector using the dideoxy sequencing method (Sanger et al., *Proc. Natl. Acad. Sci. USA* 74:5463–5467 (1977)) with the Sequenase kit (United States Biochemical) employing plasmid- and cDNA-specific primers.

Using the sequence information from each of the RACE-PCR products, the entire PGIP coding region was amplified by RNA-PCR to determine whether both RACE products belonged to the same mRNA. The nucleotide sequence of the PGIP coding region is the consensus of sequencing of both strands of three 1059-bp clones, two clones from the 3' RACE reactions, and two 569-bp clones of RNA-PCR products, and of single-stranded sequencing of four clones from the 5' RACE reaction and two 569-bp clones of genomic DNA-PCR products. Sequencing of multiple clones of many different PCR reactions makes it unlikely that errors from Taq DNA polymerase activity are included in the reported sequence.

Computer analysis indicated significant sequence similarities to only one other gene or protein in the GenBank and SwissProt data banks. A comparison with the recently published protein sequence for *Phaseolus vulgaris* PGIP is illustrated in FIG. 3. Pear PGIP is approximately 50% identical and 65% similar to bean PGIP at the amino acid level. The largest open reading frame beginning with an ATG (Met) in the pear PGIP cDNA sequence predicts a polypeptide with 330 amino acids and a molecular mass of 36.5 kD. The nucleotide sequence accurately codes for the peptide sequences, which were determined from the purified, mature pear PGIP.

Alignment of the sequences obtained by amino acid and nucleic acid sequence analyses demonstrates that the amino terminus of the mature pear PGIP is preceded by a typical 24-amino acid signal sequence, indicating probable targeting of PGIP through the endomembrane system. The potential processing site for the signal peptidase is conserved between pear and bean PGIPs.

The sequence for the processed pear PGIP has a predicted molecular mass of 33.9 kD, which is in close agreement with the observed molecular mass of the purified, deglycosylated PGIP (34 kD). The pear PGIP coding sequence contains seven potential N-glycosylation sites (Asn-X-Ser/Thr), only two of which are shared with the bean PGIP. It is interesting that all nine Cys residues of the pear PGIP are clustered at the N- and C-terminal ends of the mature protein. Eight of these are conserved with the bean PGIP. These Cys residues may affect the protein's tertiary structure. The pI of the predicted processed protein was calculated to be 6.2. All these data support the conclusion that this is an authentic PGIP cDNA sequence.

DNA Gel Blot Analysis

Genomic DNA was isolated according to Bendich et al. in *Genome Organization and Expression*, C. J. Leaver ed., pp 31–33 (1980) from pear leaves. Genomic DNA was digested with restriction endonucleases, separated on 0.8% (w/v) agarose gels in Tris-borate-EDTA buffer (Sambrook et al., supra) depurinated, denatured, and transferred to Hy-bond-N nylon membranes (Amersham) by capillary blotting. Filters were prehybridized in hybridization solution (50% formamide, 5× Denhardt's solution, 5× SSPE, 0.5% SDS, 200 µg/mL of single-stranded herring sperm DNA, 0.1% sodium pyrophosphate) before adding a $^{32}$P-radiolabeled RNA probe (1.8×10$^6$ cpm/mL, a 365-bp transcript corresponding to position 332 to 697 of FIG. 1) for hybridization at 52° C. for 48 h. Radiolabeling followed the procedures described for the Maxiscript in vitro transcription kit (Ambion, Austin, Tex.) and used the T$_7$ promoter of pCR1000. After hybridization, filters were subjected to low (Tm–25° C.) stringency washes followed by autoradiography at –80° C. using a preflashed Kodak XAR-5 film and an intensifying screen (Cronex, DuPont, Newtown, Conn.).

DNA gel blot analysis of pear genomic DNA demonstrated two hybridizing bands when DNA was digested with NsiI and NcoI and probed at low (Tm–25° C.) stringencies. The NsiI fragments were 1.25 and 3.7 kb and the NcoI fragments were 2 and 21 kb in size (data not shown). Because NsiI and NcoI did not cut within the cloned PGIP cDNA sequence and the radiolabeled probe did not span an intron, the presence of, most likely, two genes in the pear genome is suggested.

RNA Gel Blot Analysis

Total RNA was isolated from pear fruit by the method of Dong et al., (*Planta* 185:38–45 (1991)) or by a modification of the procedure of Reid et al. (*Biochem.* 27:5746–5754 (1988)). Total RNA was separated by electrophoresis in a 1.2% agarose gel containing 2.2 m formaldehyde in MOPS running buffer (Sambrook et al., supra) and blotted to Hybond-N nylon membranes. The blots were baked in a vacuum oven at 80° C., prehybridized in 5×SSPE, 50% formamide, 0.5% SDS, prehybridized in hybridization solution (as described above) with the addition of 10 ng/mL of poly(U) for 5 h, and then hybridized in fresh hybridization solution, without poly(U), with the $^{32}$P-radiolabeled RNA probe (a full-length, 1059-bp transcript, 2×10$^6$ cpm/mL) for 20 hours at 30° C. below the Tm. After hybridization, the filters were sequentially washed at 20° C. and 80° C. below the Tm and autoradiographed as described for the DNA gel blot analysis. The total amount of RNA on the blot was estimated by hybridization to an 18S rRNA probe from radish (Delseny et al., *Plant Sci. Lett.* 30:107–119 (1983)). Individual bands were quantified by densitometer scanning using a BioImage analyzer.

PGIP mRNA was approximately 100-fold more abundant in fruit than in flowers and was not detectable in pear leaves. PGIP specific activity in fruit was approximately 1400-fold higher than in leaves. On RNA gel blots, the PGIP cDNA hybridizes to an mRNA at 1.35 to 1.4 kb in total and poly(A)+ but not in poly(A)-RNA (data not shown). No other hybridizing species were detected in polyadenylated RNA even at low (Tm–30° C.) stringencies.

Discussion

The PGIP cDNA comprises an open reading frame of 330 amino acids, including a typical signal sequence for targeting to the endomembrane system, consistent with its proposed cell wall localization. The PGIP cDNA coding sequence correlates with properties that were observed in the purified PGIP: molecular mass of the processed polypeptide of approximately 34 kD, two colinear amino acid sequences that are present in the purified protein, sites for extensive glycosylation, and a pI of 6.2, which is in close agreement with the pI reported for the most abundant PGIP isoform in pear.

Comparison of the pear PGIP amino acid sequence with that recently published for bean PGIP shows only moderate amino acid sequence identity of 50%, with three regions of higher similarity (FIG. 2). Just two of seven potential glycosylation sites of pear PGIP are shared with bean PGIP. However, both sequences have highly conserved sites of potential signal peptide processing and all eight Cys residues of the bean PGIP are conserved in pear PGIP, suggesting that they may be involved in stabilizing the tertiary structure of plant PGIPs. The observed differences in PGIP primary structures may be responsible for differences in kinetics and specificity toward fungal PGs. This may be the reason why pear PGIP had little effect on *Aspergillus niger* pectinase (Sigma) activity unlike the *Phaseolus* PGIP. In addition, bean PGIP exhibits noncompetitive inhibition of *Colletotrichum lindemuthianum* endo-PG, whereas pear PGIP competitively inhibits *B. cinerea* PG (Abu-Goukh et al. (1983), supra).

The organ-specific accumulation of pear PGIP is different from that reported for PGIP mRNA accumulation in bean. Pear PGIP mRNA was detected at low levels in flowers and abundantly in fruits but was not detected in leaves, which could partially explain the differences in PGIP activity that were found in these different organs. Bean PGIP mRNA was observed in flowers, leaves, hypocotyls, and more abundantly in cell-suspension cultures. The pear PGIP promoter may differ from the bean promoter to allow for high levels of fruit-specific expression of the gene.

DNA gel blot analysis suggests the presence of at least two PGIP genes in pear. Although only a small number of PGIP genes and a single mRNA species were detected in pear using hybridization probes, it is possible that other more distantly related PGIPs exist or that other PGIPs are far less abundant in this species. Multiple PGIPs are far less abundant in this species. Multiple PGIPs have been identified in plants. Some are expressed at low levels throughout the plant, such as the bean PGIP. Others, such as the pear PGIP, show high expression in Pomoideae fruit but low or undetectable expression in other tissues. The differences in structure and expression of PGIPs from pear and bean suggest that, although these proteins inhibit fungal PGs in vitro, they may differ in their role in pectin metabolism during pathogen challenge in vivo.

Example 2

Use of pear PGIP cDNA to inhibit fungi in tomato fruit

In order to direct pear PGIP expression in tomato, the PGIP cDNA coding region was linked to promoters that direct high levels of expression. DNA containing these sequences was introduced into tomato cells, and fruit bearing plants expressing the pear PGIP sequences were regenerated. One of the promoters, 35S from Cauliflower mosaic virus (Bevan, *Nucleic Acids Res.* 12:4321 (1984)), causes expression throughout the plant, and the second, E8 (Deikman & Fischer, *EMBO J.* 7:3315 (1988)) specifies tomato fruit specific, ripening regulated expression. Agrobacterium strain LBA 4404 was used to introduce the sequences into plant cells.

The procedure followed was generally that of McCormick, *Plant Cell Reports,* 5:81–84 (1986). In brief, sterile cotyledon pieces were infected with Agrobacterium containing plasmid bearing 35SCaMV construct or a plasmid bearing the E8 construct. The infected cotyledons were placed on feeder plates; this is the co-cultivation period. The cotyledons were then moved to plates containing selection/control antibiotics and zeatin. As callus formed and plantlets regenerated, they were moved to plates containing the same antibiotics, but no hormone. Plants that rooted were transferred to larger culture vessels without antibiotics or hormone and propagated or transplanted to soil.

Transgenic tomato plants comprising the pear PGIP gene showed increased resistance to infection by *Botrytis cinerea.* In these experiments, tomato fruit were inoculated at a depth of 1 mm with $10^3$ B. cinerea spores in 10 µl water. Three days later, the number of sporulating lesions on each fruit was determined. The data for the transgenic fruit are expressed as a percent of the infection of fruit from control plants (non-transformed tomato or tomatoes transformed with constructs lacking PGIP, 1—1 and 1–6). The results are shown in FIG. 4.

Example 3

Molecular Characterization of a Polygalacturonase Inhibitor from Tomato

Protein purification

Pericarp tissue from mature green tomato (*L. esculentum* Mill. cv. Sunny) fruits was homogenized in 1 l of extraction buffer (20 mM Na-acetate, pH 5.2) per kg fresh weight of fruit tissue. The homogenate was centrifuged at 27,000× g for 15 min at 4° C. The pellet was resuspended in 1 l of extraction buffer containing 1M NaCl and stirred for 30 min at 4° C. After centrifugation (27,000× g, 15 min), the supernatant was saved while the pellet was re-extracted in the 1M NaCl-containing buffer. The combined 1M NaCl supernatants were concentrated by ultrafiltration through a PM-10 membrane (Amicon, Danvers, Mass.).

The concentrated extract was applied to a concanavalin A (Con A) Sepharose 4B column and separated as in Example 1. Fractions which contained PGIP activity eluted in both the flow-through and with 0.25M α-methyl mannoside. Unbound and bound fractions were dialyzed separately against 50 mM Na-acetate, pH 5.2 and concentrated by ultra filtration.

These two protein preparations were purified further by cation-exchange fast performance liquid chromatography (FPLC; Pharmacia, Uppsala, Sweden) using a Mono S HR 5/5 column as described above. Fractions containing PGIP activity were pooled and the buffer of the active material changed to 20 mM Tris, pH 8.0 (buffer A) using a Centricon-10 microconcentrator. Proteins were separated by anion-exchange FPLC (Mono Q HR 5/5) using a linear NaCl gradient (20 ml, to a final concentration of 0.35M NaCl in buffer A) Active fractions were pooled and stored at –20° C.

PGIP activity assay

*B. cinerea* DEL 11 (obtained from Richard M. Bostock, Department of Plant Pathology, University of California, Davis) was used to measure inhibition of PG activity as described above.

Protein assay

Protein was determined using a bicinchoninic (BCA) acid protein assay kit (Pierce, Rockford, Ill.) and BSA as a standard.

Deglycosylation of proteins

PGIP preparations were deglycosylated enzymatically using peptide N-glycosidase F (Boehringer, Mannheim, FRG) according to the manufacturer's instructions. Protein samples were heat denatured at 100° C. for 3 min in 150 mM Tris, pH 8, 5 mM EDTA and 0.1M β-mercaptoethanol in the presence of 0.5% (w/v) SDS Nonidet P-40 was added to a final concentration of 1.25% (v/v) prior to addition of the enzyme (0.12 U/µg PGIP). The samples were incubated at 37° C. for 17h. Samples which were treated with endoglycosidase II (Boehringer, Mannheim, FRG) were boiled for 3 min in 100 mM Na-acetate, pH 6.0.1M β-mercaptoethanol containing a 1.2-fold molar excess of SDS relative to protein content. After adding PMSF (0.5 mM) and enzyme (0.17 mU/µg PGIP), the samples were incubated at 37° C. for 17 h.

Chemical deglycosylation of PGIP preparations was performed according to Karp et al. *J. Biol. Chem.* 257:7330–7335 (1982) using trifluoromethane sulfonic acid (TFMS).

Protein gel electrophoresis

Proteins were separated by SDS-PAGE and the gels were silver stained using standard techniques.

Non-equilibrium pH gradient electrophoresis (NEPHGE) was performed under non-denaturing conditions in vertical slab gels (4% acrylamide) using standard techniques. The gradient was generated using pH 3.5–10 ampholines (LKB, Uppsala, Sweden). Standard proteins of known pIs (BioRad, Richmond, Calif.) were separated to determine the profile of the pH gradient. Gels were stained with Coomassie Blue G-Colloidal according to the manufacturer's instructions (Sigma, St. Louis, Mo.).

Proteolytic cleavage and amino acid sequencing

Purified PGIP (20 µg) was reduced and alkylated prior to proteolytic digestion using endoproteinase Lys-C according to Stone et al. in *A Practical Guide to Protein and Peptide Purification for Microsequencing* Matsudaira, PT ed., pp 31–47 (Academic Press, San Diego, Calif. 1989) with modifications. Lyophilized protein was dissolved in 25 mM Tris, pH 8.5, 8M urea, 1 mM EDTA. Following an addition of DTT to a final concentration of 11 mM, the sample was purged with nitrogen and incubated at 37° C. for 2 h. Iodoacetamide was added to a final concentration of 22 mM and the sample was incubated for 30 min in the dark. The reduced and alkylated protein preparation was diluted with 6 volumes of 25 mM Tris, pH 8.5, 1 mM EDTA. Endoproteinase Lys-C (0.4 µg; Boehringer, Mannheim, FRG) was added and incubation was at 37° C. for 17h.

The generated peptide fragments were separated on an Aquapore RP-300 column (100×2.1 mm; Applied Biosystems, Foster City, Calif.) using a Hewlett-Packard HP 1090 HPLC with a linear gradient of 0 to 50% acetonitrile in 0.1% TFA for 75 min. at a flow rate of 0.5 ml/min. Peptide peaks were detected at 210 nm and fractions were collected manually based on the detector signal.

Purified PGIP and peptide fragments were sequenced by automated Edman degradation according to standard techniques.

Isolation of a genomic clone encoding tomato PGIP

N-terminal (VRXNPKDKKVLLQIDDI (Seq. I.D. No.: 17) GNPYHI (Seq. I.D. No.: 18), ASXDPN (Seq. I.D. No.: 19), and internal amino acid sequences (DLGN- PYHLASXDPNTDCCY (Seq. I.D. No.: 20) and LTGTI- PESFGRFK (Seq. I.D. No.: 21), were determined. Primers 1 (5'-CARATHAARAARGAYTIRGG-3', Seq. I.D. No.: 22), 2 (5' GGAATTCGAYCCNAAYACNGAYTGYTG-3', Seq. I.D. NO.: 23), and 3 (5'-CCRAANGAYTCNGGDAT- NGT-3', Seq. I.D. No.: 24) were synthesized (Applied Biosystems, Foster City, Calif.), (N=A, T, C, or G; Y=T or C; R=A or G; H=A, T, or C; and D=A, T, or G). cDNA was obtained by reverse transcription of 100 ng of poly (A$^+$) RNA from mature green stage 3 (MG3, green flesh with liquid locule contents) tomato (*L. esculentum* cv. Castemart) fruit using random hexamers. One-fifth of the first strand cDNA reaction or 1 µg genomic DNA was used as a template in polymerase chain reactions (PCR) with primers 1 and 3. The reactions were carried out in a Perkin-Elmer Cetus (Norwalk, Conn.) DNA thermal cycler using Taq DNA polymerase (Perkin-Elmer, Cetus) for 5 cycles (one cycle=1 rain at 94° C., 2 min at 37° C., and 2 min at 72° C. and 30 cycles (one cycle=1 min at 94° C., 90 s at 42° C., and 2 min at 72° C.) according to the manufacturer's instructions. A second PCR was carried out using one-tenth of the products from the first PCR and primers 2 and 3 for 5 cycles (one cycle=1 min at 94° C., 1 min at 37° C., and 1 min at 72° C.) and 30 cycles (one cycle=1 min at 94° C., 1 min at 42° C., and 1 min at 72° C.). The resulting 417 bp products were gel purified and ligated into pBluescrip K5$^+$ (Stratagene, San Diego, Calif.).

A library of tomato (*L. esculentum* cv. VFNT Cherry) genomic DNA in the vector Charon 35 (obtained from Robert L. Fisher, Department of Plant Biology, University of California, Berkeley) was screened by plague hybridization with the $^{32}$p-labeled labeled 417 bp PCR product. Phage DNA was prepared by liquid lysis, digested with restriction endonucleases and subcloned into pBluescript KS$^+$. All PCR products and genomic subclones were sequenced in pBluescript KS$^+$ by dideoxy sequencing with the Sequenase kit (United States Biochemical, Cleveland, Ohio) employing plasmid- and gene-specific primers.

Southern blotting

Genomic DNA was isolated from tomato leaves according to Bernatzky and Tanksley *Theor. Appl. Genet.* 72:314–321 (1986). Genomic DNA was digested with restriction endonucleases, separated in 0.8 % agarose gels, depurinated, denatured and transferred to Hybond-N (Amersham, Arlington Heights, Ill.). The 417 bp PCR product was $^{32}$P-labeled by random priming and used for hybridization in 50% formamide, 5× SPPE, 5× Denhardt's solution, 0.5% SDS, 0.05% sodium pyrophosphate, and 200 µg/ml single stranded salmon sperm DNA at 42° C. for 24 h. Final washing conditions were 2× SSC, 0.1% (w/v) SDS, 42° C.

Northern blotting

Total RNA was isolated from tomato fruit (*L. esculentum* cv. Castlemart) and cell suspension cultures (*L. esculentum* cv. VENT Cherry). Poly (A$^+$) RNA was selected using Dynabeads Oligo (dT)$_{25}$ (Dynal, Great Neck, N.Y.). Poly (A$^+$) RNA was separated in 1.2% agarose gels containing 2.2M formaldehyde and transferred to Hybond-N. The $^{32}$P-labeled PCR product was used for hybridization as described for Southern blotting, with the exception that incubation was at 50° C. Final washing conditions were 0.2× SSC, 0.1% SDS, 55° C.

RESULTS

Post-translational modification of tomato PGIP

Con A chromatography of proteins extracted from pericarp tissue of tomato fruit resulted in the identification of two distinct PGIPs. Whereas the majority of PGIP activity was bound by Con A (PGIP A), a minor fraction (less than 10%) eluted in the application buffer (PGIP B). PGIP B was reapplied to the column and still eluted in the flow-through, suggesting that the failure to bind was due to the carbohydrate properties of PGIP B rather than to limited column capacity. PGIPs A and B were purified further by cation and anion exchange FPLC.

Analysis of the resulting protein preparations by SDS-PAGE followed by silver staining demonstrated that while PGIP A was purified to apparent homogeneity, PGIP B was only partially purified. The latter protein preparation contained at least 3 polypeptides with different molecular masses. The most abundant protein (35 kD) was identified as PGIP B by its cross reactivity with a polyclonal antibody raised against deglycosylated, purified pear PGIP (PGIP A was also recognized by the antibody). Edman degradation of the 35 kD band yielded two distinct sequences, the shorter one of which was identical to PGIP A over four amino acids (Val-Arg-X-Asn), suggesting that PGIP's A and B are similar polypeptides with differences in glycosylation.

The effects of enzymatic and chemical deglycosylation of tomato and pear PGIPs were compared to determine potential differences in post-translational modification. Tomato PGIP A glycoprotein migrated as a diffuse band with molecular mass ranging from 35 to 41 kD. After treatment with Endo H, a minor change in mobility was observed. PNGase F, however, removed the majority of carbohydrates associated with PGIP A and caused the appearance of a peptide doublet of 35 and 37 kD. Chemical deglycosylation of PGIP A produced a single band of 34 kD. Since PGIP A was much more susceptible to PNGase F than to Endo H, most of the N-linked carbohydrates association with PGIP A appear to be of the complex type. In contrast, PNGase F treatment only partially deglycosylated pear PGIP resulting in a reduction in molecular mass from 43 kD to 39 kD. Chemical deglycosylation of pear PGIP produced a protein band of 34 kD, the molecular mass expected from the sequence of the processed polypeptide. Thus, PNGase F removed relatively fewer carbohydrates from pear PGIP than tomato PGIP A. Taken together these results suggest that N-linked glycosylation differs between tomato and pear PGIPs. The observation that enzymatic treatments were less effective than chemical deglycosylation in reducing molecular mass suggests that some of the N-linked glycans are not accessible to either Endo H or PNGase F, or that O-glycosylation occurs as well.

Figure 5:
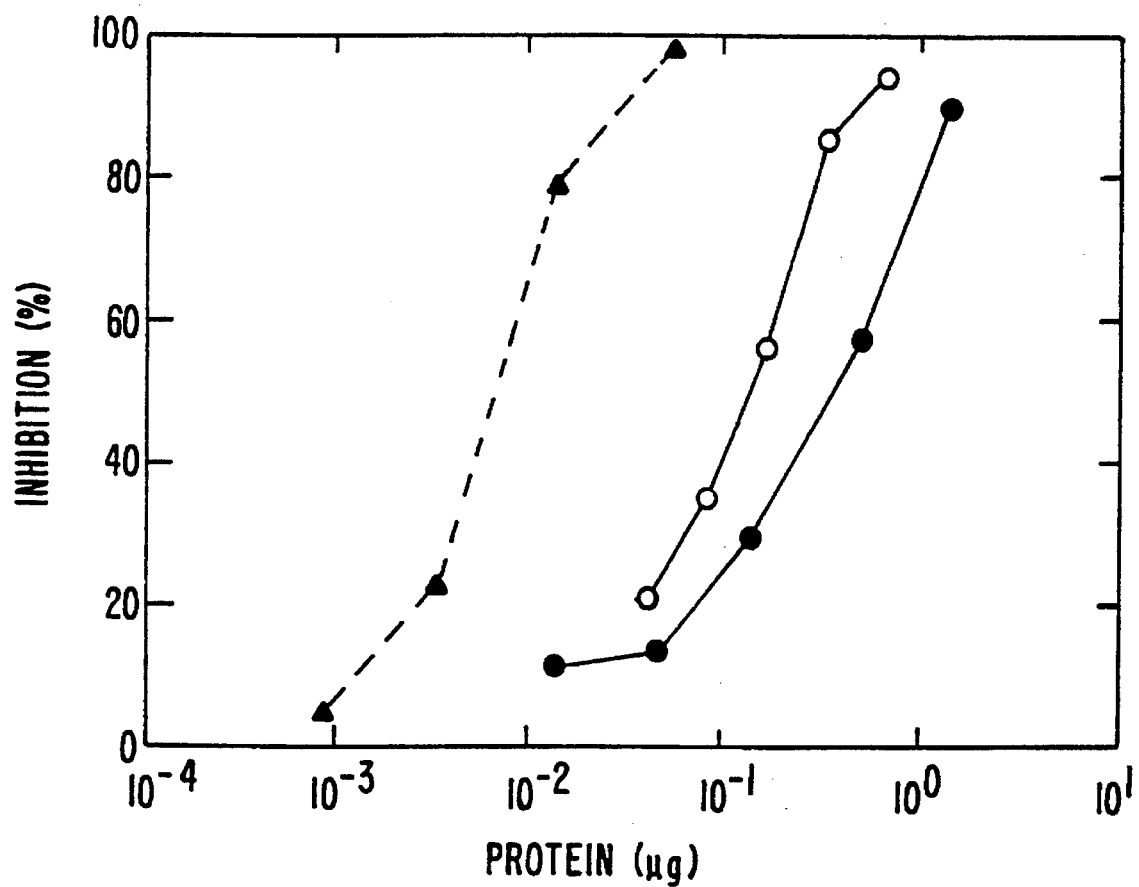
FIG. 5 shows inhibition of B. cinerea PG by tomato and pear PGIPs. Culture filtrate with a PG activity of 0.65 µmol/min was incubated with sodium polypectate in the absence or presence of different concentrations of pear PGIP (▲), tomato PGIP A (○), and PGIP B (●) and analyzed for reducing sugars. Protein concentrations were determined by amino acid analysis of the purified proteins (pear PGIP and tomato PGIP A), or by BCA assay (tomato PGIP B).

The isoelectric point of tomato PGIP A was determined by NEPHGE. Separation of native PGIP A by NEPHGE resulted in a major band of pI 9.0 and a minor band of pI 8.8. The minor band could either be a PGIP charge isoform because of its small difference in pI or merely a contamination protein. No contaminating bands were identified, however, in the silver stained SDS-PAGE gel of a lesser amount of PGIP A suggesting that the protein of pI 8.8 has a similar molecular mass. PG from *B. cinerea* is more strongly inhibited by pear PGIP than tomato PGIP PG from *B. cinerea* was incubated with different concentrations of purified pear PGIP, tomato PGIP A, or partially purified tomato PGIP B and the release of reducing sugars was measured (FIG. 5). Pear PGIP was approximately 20 times more active against *B. cinerea* PG than either of the tomato PGIPs. The approximately 2 to 3 fold different in apparent inhibitory specific activity between tomato PGIPs A and B is most likely due to contaminating proteins in the PGIP B preparation (see above) rather than differences in glycosylation indicated by differential binding to Con A. This may suggest that the glycans present in PGIP A are not required for PG inhibitory activity. It was also observed that pear PGIP treated with PNGase F in the absence of SDS had a reduced molecular mass but unchanged PGIP specific activity (dam not shown). These data show that PGIPs purified from different plant species can differ in their inhibition of specific fungal PGs.

Isolation of a PGIP genomic clone

Purified tomato PGIP A and its HPLC-purified, Lys-C generated peptides were subjected to amino acid sequence analysis. Degenerate oligonucleotide primers were synthesized and used in PCR to amplify 417 bp products from genomic DNA and MG3 tomato fruit cDNA. The nucleotide sequences obtained from both sources were identical. The PCR products were used as probes to screen a tomato genomic library. Two positive clones which were indistinguishable in their restriction enzyme patterns were obtained by analyzing $5 \times 10^5$ plaques. A 2075 bp Xba 1 fragment that contained the entire PGIP open-reading frame and a portion of the 5' and 3' untranslated regions of the gene was sequenced from both strands (FIG. 2). The PGIP coding sequence is not interrupted by introns. The 420 nucleotide sequence preceding the translational start codon contains several putative TATA-boxes. The longest open-reading frame comprises 984 nucleotides. A putative polyadenylation signal is located 140 nucleotides downstream of the translational stop codon. A comparison of the nucleotide sequences of the 417 bp PCR products and the 2075 bp genomic clone revealed a single nucleotide substitution (at position 595 of the Xba 1 fragment) which resulted in a conservative amino acid change, Ile for Val. Because the PCR products and genomic clone were derived from different cultivars, cv, Castlemart and cv, VFNT, Cherry, respectively, this difference may reflect cultivar differences.

The deduced amino acid sequence of the genomic clone accurately codes for the peptide sequences which were determined by Edman degradation of purified tomato PGIP A and its Lys-C fragments. A comparison with published sequences for the bean and pear PGIPs (FIG. 3) revealed the conservation of a potential cleavage site for signal peptidase. The mature polypeptide sequence of tomato PGIP is more closely related to pear PGIP-(68% identity) than to bean PGIP (50% identity). The N- and C-terminal regions are more highly conserved than are other parts of the protein. Eight cysteine residues were conserved between these different species, suggesting the existence of disulfide bonds. The existence of this type of modification was supported by the observation that reductive carboxymethylation of the cysteine residues of tomato PGIP A was necessary for proteolysis by Lys C.

Tomato PGIP contained seven potential N-glycosylation sites (Asn-X-Ser/Thr), two of which are conserved between all three PGIPs and three additional ones which are shared with pear PGIP. The predicted molecular mass of the mature polypeptide was 34.3 kD which is in good agreement with the molecular mass of the chemically deglycosylated tomato PGIP A (34 kD). The predicted pI of the processed polypeptide was calculated to be 8.4 and is in agreement with the basic nature of native tomato PGIP A (pI 9.0). Collectively, these data support the conclusion that the genomic sequence codes for PGIPs that are expressed in tomato fruit.

Figure 6A:
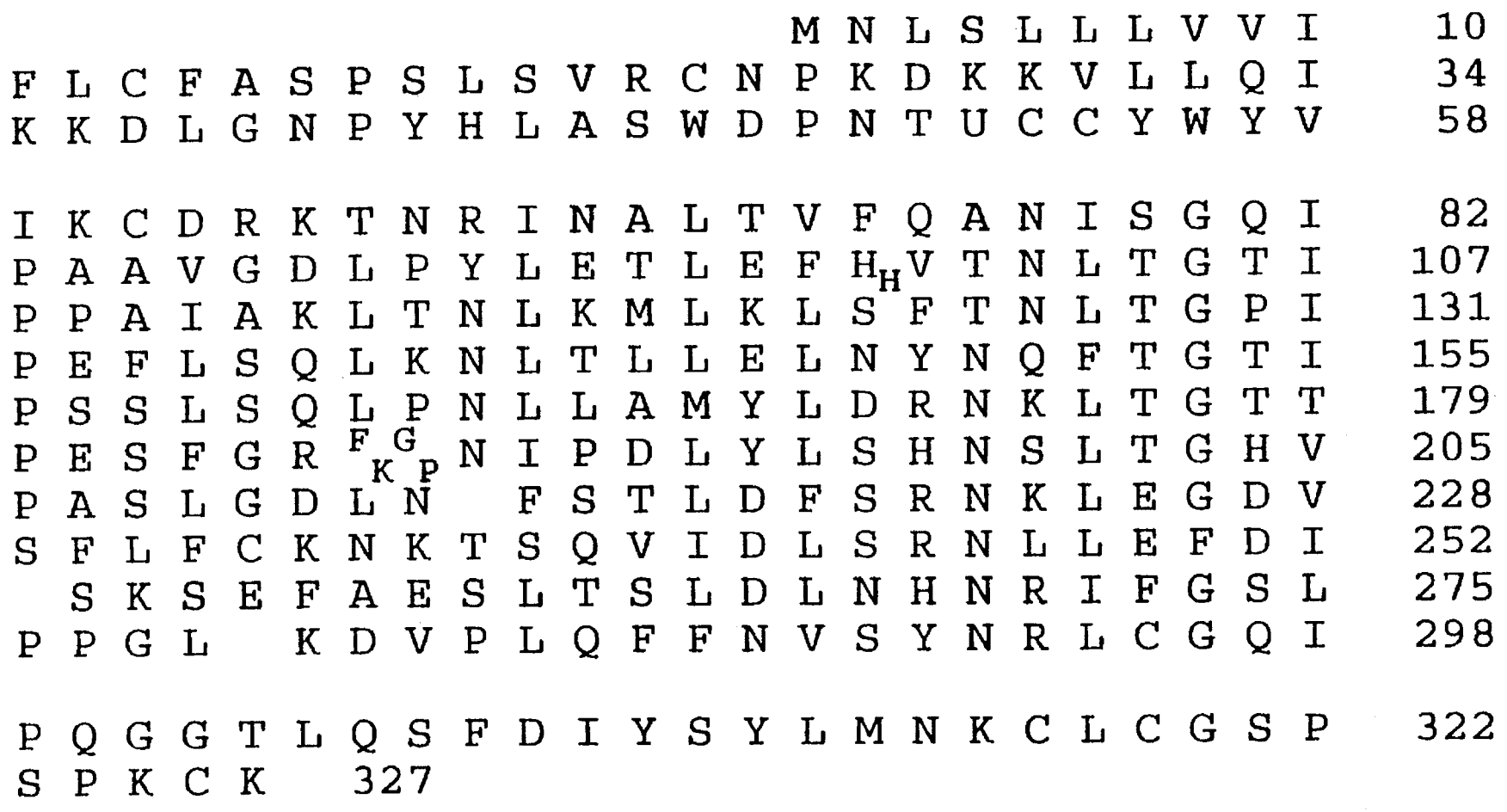

The deduced amino acid sequence of tomato PGIP was compared to sequences in the GenBank and SwissProt data bases and homologies to a family of proteins which contain leucine-rich repeats were identified. A block of 10 tandem leucine-rich repeats with an average length of 24 amino acids is present in PGIPs from tomato bean and pear (FIG. 6A).

PGIP sequences from bean, pear and tomato contain a motif of leucine-rich repeats. The consensus sequence of this repeating motif (FIG. 6B) is related to leucine-rich repeats that are found in proteins with divergent functions from Drosophila, humans, yeast, and plants. Similar motifs are present in several proteins that interact with other polypeptides. Thus, the leucine-rich repeats may be required for the interaction with and inhibition of PG. Despite the conservation of this consensus sequence, this region is more variable than the N- and C- terminal portions of the proteins and may be responsible for the observed differences in kinetics of the proteins. Southern and northern blot analysis Tomato genomic DNA was analyzed by Southern blotting. Of the restriction enzymes used (Bam HI, Cla1, EcoRI, HindIII, and ScaI) only EcoRI cut within the radiolabeled probe that was used for hybridization. However, all restriction enzymes but Sca1 yielded at least two hybridizing fragments, suggesting the presence of a second PGIP gene per haploid tomato genome.

Northern blot analysis indicated that the fractional abundance of PGIP mRNA relative to poly $(A^+)$ RNA was similar in immature and ripening fruits, and in cell suspension cultures. The size of the PGIP mRNA was estimated to be 1.35 kb. PGIP activity was not detected in extracts from tomato leaves, although mRNA levels were not assayed in this tissue.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated DNA construct comprising a polynucleotide sequence encoding a pear polygalacturonase inhibitor protein (PGIP), wherein the polynucleotide sequence hybridizes to SEQ. ID. No. 1 under hybridization conditions which include washing at 55° C. and 0.2× SSC.

2. The DNA construct of claim 1, wherein the polynucleotide sequence is as shown in SEQ. ID. NO. 1.

3. An isolated DNA construct comprising a polynucleotide sequence encoding a tomato polygalacturonase inhibitor protein (PGIP), wherein the polynucleotide sequence hybridizes to SEQ. ID. NO. 3 under hybridization conditions which include washing at 55° C. and 0.2× SSC.

4. The DNA construct of claim 3, wherein the polynucleotide sequence is as shown in SEQ. ID. No. 3.

5. The DNA construct of claim 1, wherein the polynucleotide sequence is a full length PGIP gene.

6. The DNA construct of claim 1 or claim 3, further comprising a promoter operably linked to the polynucleotide sequence.

7. The DNA construct of claim 6, wherein the promoter is a plant promoter.

8. The DNA construct of claim 7, wherein the promoter is a fruit-specific promoter.

9. A transgenic plant comprising a recombinant expression cassette comprising a plant promoter operably linked to the polynucleotide sequence of claim 1 or claim 3.

10. The transgenic plant of claim 9, wherein the plant promoter is a heterologous promoter.

11. The transgenic plant of claim 9, wherein the plant is tomato.

12. The transgenic plant of claim 9, wherein the plant is strawberry.

13. The transgenic plant of claim 9, wherein the polynucleotide sequence confers resistance to Botrytis cinerea.

14. The transgenic plant of claim 9, wherein the polynucleotide sequence of SEQ. ID. No. 1.

15. The transgenic plant of claim 9, wherein the polynucleotide sequence is SEQ. ID. No. 3.

16. A method of conferring resistance to fungal infection in a plant, the method comprising:

introducing into plant tissue a recombinant expression cassette comprising a plant promoter operably linked to the polynucleotide sequence of claim 1 or claim 3;

regenerating the plant tissue into a whole plant, whereby the regenerated plant transcribes the polynucleotide sequence; and selecting plants which are resistant to fungal infection.

17. The method of claim 16, wherein the plant tissue is from tomato.

18. The method of claim 16, wherein the plant tissue is from strawberry.

19. The method of claim 16, wherein the recombinant expression cassette is introduced into the plant tissue using Agrobacterium.

20. The method of claim 16, wherein the polynucleotide sequence is as shown SEQ. ID. No. 1 or SEQ. ID. No. 3.

21. The method of claim 16, wherein the promoter is a fruit-specific promoter.

22. The method of claim 16, wherein the promoter is a flower-specific promoter.

23. A method of isolating a PGIP gene from a plant, the method comprising probing a DNA library prepared from the plant with a polynucleotide sequence selected from the group consisting of from SEQ. ID. No. 1 and SEQ. ID. No. 3.

24. The method of claim 23, wherein the DNA library comprises cDNA.

25. An isolated DNA construct comprising a polynucleotide sequence encoding a pear polygalacturonase inhibitor protein (PGIP), having an amino acid sequence as shown in SEQ. ID. No. 2.

26. An isolated DNA construct comprising a polynucleotide sequence encoding a tomato polygalacturonase inhibitor protein (PGIP), having an amino acid sequence as shown in SEQ. ID. No. 4.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 1058 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 34..1023

( i x ) FEATURE:
    ( A ) NAME/KEY: misc_feature
    ( B ) LOCATION: 1..1058
    ( D ) OTHER INFORMATION: /standard_name="Pear PGIP cDNA"

( x i ) SEQUENCE DESCRIPTION: SEQ ID NO:1:

```
ACATCTCTCA GGCTCTCAAC CAAAACCAAA ACA ATG GAA CTC AAG TTC TCC ACC           54
                                     Met Glu Leu Lys Phe Ser Thr
                                      1               5

TTC CTC TCC CTA ACC CTA CTC TTC TCC TCC GTC CTA AAC CCC GCT CTC           102
Phe Leu Ser Leu Thr Leu Leu Phe Ser Ser Val Leu Asn Pro Ala Leu
         10              15                  20

TCC GAT CTC TGC AAC CCC GAC GAC AAA AAA GTC CTC CTA CAA ATC AAG           150
Ser Asp Leu Cys Asn Pro Asp Asp Lys Lys Val Leu Leu Gln Ile Lys
 25              30                  35

AAA GCC TTC GGC GAC CCC TAC GTC TTG GCC TCA TGG AAA TCA GAC ACT           198
Lys Ala Phe Gly Asp Pro Tyr Val Leu Ala Ser Trp Lys Ser Asp Thr
 40              45                  50                       55

GAC TGC TGC GAT TGG TAC TGC GTC ACC TGT GAC TCC ACC ACA AAC CGC           246
Asp Cys Cys Asp Trp Tyr Cys Val Thr Cys Asp Ser Thr Thr Asn Arg
                 60                  65                  70

ATT AAC TCC CTC ACC ATC TTT GCC GGC CAG GTG TCA GGC CAA ATC CCC           294
Ile Asn Ser Leu Thr Ile Phe Ala Gly Gln Val Ser Gly Gln Ile Pro
             75                  80                  85

GCC CTA GTA GGA GAC TTG CCA TAC CTT GAA ACC CTT GAA TTC CAT AAG           342
Ala Leu Val Gly Asp Leu Pro Tyr Leu Glu Thr Leu Glu Phe His Lys
         90                  95                 100

CAA CCC AAT CTC ACT GGC CCA ATC CAA CCC GCC ATT GCC AAG CTC AAA           390
Gln Pro Asn Leu Thr Gly Pro Ile Gln Pro Ala Ile Ala Lys Leu Lys
105                 110                 115

GGA CTC AAG TCT CTC AGG CTC AGC TGG ACC AAC CTC TCA GGC TCT GTC           438
Gly Leu Lys Ser Leu Arg Leu Ser Trp Thr Asn Leu Ser Gly Ser Val
120                 125                 130                 135

CCT GAC TTC CTC AGC CAA CTC AAG AAC CTC ACA TTC CTC GAC CTC TCC           486
Pro Asp Phe Leu Ser Gln Leu Lys Asn Leu Thr Phe Leu Asp Leu Ser
                140                 145                 150

TTC AAC AAC CTC ACC GGT GCC ATC CCC AGC TCG CTT TCT GAG CTC CCA           534
Phe Asn Asn Leu Thr Gly Ala Ile Pro Ser Ser Leu Ser Glu Leu Pro
            155                 160                 165

AAC CTC GGC GCT CTT CGT CTA GAC CGC AAT AAG CTC ACA GGT CAT ATT           582
Asn Leu Gly Ala Leu Arg Leu Asp Arg Asn Lys Leu Thr Gly His Ile
        170                 175                 180

CCG ATA TCG TTT GGG CAG TTC ATT GGC AAC GTT CCA GAC CTG TAT CTC           630
Pro Ile Ser Phe Gly Gln Phe Ile Gly Asn Val Pro Asp Leu Tyr Leu
185                 190                 195

TCC CAC AAC CAG CTT TCT GGT AAC ATT CCA ACC TCA TTC GCT CAG ATG           678
Ser His Asn Gln Leu Ser Gly Asn Ile Pro Thr Ser Phe Ala Gln Met
200                 205                 210                 215

GAC TTC ACC AGC ATA GAC TTA TCA CGG AAC AAG CTC GAA GGT GAC GCA           726
Asp Phe Thr Ser Ile Asp Leu Ser Arg Asn Lys Leu Glu Gly Asp Ala
                220                 225                 230

TCC GTG ATA TTT GGG CTG AAC AAG ACA ACC CAG ATT GTG GAC CTG TCC           774
Ser Val Ile Phe Gly Leu Asn Lys Thr Thr Gln Ile Val Asp Leu Ser
            235                 240                 245

AGG AAC TTG CTG GAA TTT AAT CTG TCA AAG GTG GAG TTT CCG ACA AGC           822
Arg Asn Leu Leu Glu Phe Asn Leu Ser Lys Val Glu Phe Pro Thr Ser
```

|  |  |  |  |  |  |  |  |  |  |  |  |  |  |  |  |
|---|---|---|---|---|---|---|---|---|---|---|---|---|---|---|---|
|  |  |  | 250 |  |  |  |  | 255 |  |  |  |  | 260 |  |  |
| TTG | ACC | TCG | GTG | GAT | ATC | AAC | CAC | AAT | AAG | ATC | TAC | GGG | AGT | ATC | CCA |
| Leu | Thr | Ser | Val | Asp | Ile | Asn | His | Asn | Lys | Ile | Tyr | Gly | Ser | Ile | Pro |
|  | 265 |  |  |  |  |  | 270 |  |  |  |  | 275 |  |  |  |

870

GTG GAG TTT ACG CAA CTG AAT TTC CAG TTC CTG AAC GTG AGC TAC AAC     918
Val Glu Phe Thr Gln Leu Asn Phe Gln Phe Leu Asn Val Ser Tyr Asn
280                     285                 290                 295

AGG CTG TGT GGT CAG ATT CCT GTG GGT GGA AAG TTG CAG AGC TTC GAC     966
Arg Leu Cys Gly Gln Ile Pro Val Gly Gly Lys Leu Gln Ser Phe Asp
            300                 305                 310

GAG TAT TCT TAT TTC CAT AAC CGA TGC TTG TGC GGT GCT CCA CTC CCA    1014
Glu Tyr Ser Tyr Phe His Asn Arg Cys Leu Cys Gly Ala Pro Leu Pro
                315                 320                 325

AGC TGC AAG  TAAAGGCCAC  AACTGCAGAT  TTGGCCAGCA  ATTTT             1058
Ser Cys Lys
        330

(2) INFORMATION FOR SEQ ID NO:2:

(i) SEQUENCE CHARACTERISTICS:
      (A) LENGTH: 330 amino acids
      (B) TYPE: amino acid
      (D) TOPOLOGY: linear (ii) MOLECULE TYPE: protein (xi) SEQUENCE DESCRIPTION: SEQ ID NO:2:

Met Glu Leu Lys Phe Ser Thr Phe Leu Ser Leu Thr Leu Leu Phe Ser
 1               5                  10                  15

Ser Val Leu Asn Pro Ala Leu Ser Asp Leu Cys Asn Pro Asp Asp Lys
            20                  25                  30

Lys Val Leu Leu Gln Ile Lys Lys Ala Phe Gly Asp Pro Tyr Val Leu
            35                  40                  45

Ala Ser Trp Lys Ser Asp Thr Asp Cys Cys Asp Trp Tyr Cys Val Thr
        50                  55                  60

Cys Asp Ser Thr Thr Asn Arg Ile Asn Ser Leu Thr Ile Phe Ala Gly
 65                  70                  75                  80

Gln Val Ser Gly Gln Ile Pro Ala Leu Val Gly Asp Leu Pro Tyr Leu
                 85                  90                  95

Glu Thr Leu Glu Phe His Lys Gln Pro Asn Leu Thr Gly Pro Ile Gln
            100                 105                 110

Pro Ala Ile Ala Lys Leu Lys Gly Leu Lys Ser Leu Arg Leu Ser Trp
            115                 120                 125

Thr Asn Leu Ser Gly Ser Val Pro Asp Phe Leu Ser Gln Leu Lys Asn
    130                 135                 140

Leu Thr Phe Leu Asp Leu Ser Phe Asn Asn Leu Thr Gly Ala Ile Pro
145                 150                 155                 160

Ser Ser Leu Ser Glu Leu Pro Asn Leu Gly Ala Leu Arg Leu Asp Arg
                165                 170                 175

Asn Lys Leu Thr Gly His Ile Pro Ile Ser Phe Gly Gln Phe Ile Gly
            180                 185                 190

Asn Val Pro Asp Leu Tyr Leu Ser His Asn Gln Leu Ser Gly Asn Ile
        195                 200                 205

Pro Thr Ser Phe Ala Gln Met Asp Phe Thr Ser Ile Asp Leu Ser Arg
    210                 215                 220

Asn Lys Leu Glu Gly Asp Ala Ser Val Ile Phe Gly Leu Asn Lys Thr
225                 230                 235                 240

Thr Gln Ile Val Asp Leu Ser Arg Asn Leu Leu Glu Phe Asn Leu Ser

|     |     |     |     | 245 |     |     |     |     | 250 |     |     |     |     | 255 |     |
| --- | --- | --- | --- | --- | --- | --- | --- | --- | --- | --- | --- | --- | --- | --- | --- |
| Lys | Val | Glu | Phe 260 | Pro | Thr | Ser | Leu | Thr 265 | Ser | Val | Asp | Ile | Asn 270 | His | Asn |
| Lys | Ile | Tyr 275 | Gly | Ser | Ile | Pro | Val 280 | Glu | Phe | Thr | Gln | Leu 285 | Asn | Phe | Gln |
| Phe | Leu 290 | Asn | Val | Ser | Tyr | Asn 295 | Arg | Leu | Cys | Gly | Gln 300 | Ile | Pro | Val | Gly |
| Gly 305 | Lys | Leu | Gln | Ser | Phe 310 | Asp | Glu | Tyr | Ser | Tyr 315 | Phe | His | Asn | Arg | Cys 320 |
| Leu | Cys | Gly | Ala | Pro 325 | Leu | Pro | Ser | Cys | Lys 330 |     |     |     |     |     |     |

( 2 ) INFORMATION FOR SEQ ID NO:3:

( i ) SEQUENCE CHARACTERISTICS:
        ( A ) LENGTH: 2075 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 421..1401

( x i ) SEQUENCE DESCRIPTION: SEQ ID NO:3:

| | | | | | | |
|---|---|---|---|---|---|---|
| CTAGACAAAC | TTTACCCAGG | GAAGGTGTCA | TCTTAAATCA | ATCAAAATAT | ATATTTTTCA | 60 |
| TCCTAAACTC | ACTTAAATAA | AAAAGAATCT | ATTCTTACTT | AAACACTTAA | CATTTTTAAA | 120 |
| AACATTTTCA | TTTTAGTATC | CTTTTATTTT | ATAATCAATT | TAATTAAAAT | ATCTATGAAT | 180 |
| ATAAACATCA | TGATTAATAA | ATTGTAAAAT | CATTGGACAT | CTCTTTTGAA | GTTTGAATTT | 240 |
| CAAAAGCCAA | CGCATTATAT | TCTTAGATAC | TGATACACAC | CATGTGACTA | GTGACTTGTG | 300 |
| GGGCAGTTTT | TCTTGACCAA | AAATCCGTAT | TGCTAAAATA | TGACCCTTTT | TTTTGTTTTA | 360 |
| TAAATACCAA | TGAGCTAAGT | TATAATATAA | TATTGTTCAT | AAACAAAAAA | AAAAAAAAAT | 420 |

| ATG | AAC | TTG | TCT | CTT | CTT | CTT | GTA | GTT | ATT | TTT | CTT | TGC | TTT | GCT | TCT | 468 |
|---|---|---|---|---|---|---|---|---|---|---|---|---|---|---|---|---|
| Met | Asn | Leu | Ser | Leu | Leu | Leu | Val | Val | Ile | Phe | Leu | Cys | Phe | Ala | Ser | |
| 1 | | | | 5 | | | | | 10 | | | | | 15 | | |

| CCT | TCA | CTA | TCA | GTA | AGA | TGC | AAT | CCG | AAA | GAC | AAA | AAA | GTC | CTT | CTA | 516 |
|---|---|---|---|---|---|---|---|---|---|---|---|---|---|---|---|---|
| Pro | Ser | Leu | Ser | Val | Arg | Cys | Asn | Pro | Lys | Asp | Lys | Lys | Val | Leu | Leu | |
| | | | 20 | | | | | 25 | | | | | 30 | | | |

| CAA | ATA | AAG | AAA | GAC | TTA | GGC | AAT | CCT | TAC | CAT | TTA | GCT | TCA | TGG | GAT | 564 |
|---|---|---|---|---|---|---|---|---|---|---|---|---|---|---|---|---|
| Gln | Ile | Lys | Lys | Asp | Leu | Gly | Asn | Pro | Tyr | His | Leu | Ala | Ser | Trp | Asp | |
| | | 35 | | | | | 40 | | | | | 45 | | | | |

| CCA | AAC | ACA | GAT | TGC | TGT | TAC | TGG | TAC | GTC | ATA | AAA | TGT | GAC | CGG | AAA | 612 |
|---|---|---|---|---|---|---|---|---|---|---|---|---|---|---|---|---|
| Pro | Asn | Thr | Asp | Cys | Cys | Tyr | Trp | Tyr | Val | Ile | Lys | Cys | Asp | Arg | Lys | |
| | 50 | | | | | 55 | | | | | 60 | | | | | |

| ACC | AAC | CGG | ATA | AAT | GCT | CTC | ACC | GTC | TTC | CAA | GCC | AAT | ATC | TCC | GGC | 660 |
|---|---|---|---|---|---|---|---|---|---|---|---|---|---|---|---|---|
| Thr | Asn | Arg | Ile | Asn | Ala | Leu | Thr | Val | Phe | Gln | Ala | Asn | Ile | Ser | Gly | |
| 65 | | | | | 70 | | | | | 75 | | | | | 80 | |

| CAA | ATT | CCG | GCA | GCC | GTC | GGA | GAC | CTT | CCA | TAT | CTC | GAA | ACA | TTG | GAA | 708 |
|---|---|---|---|---|---|---|---|---|---|---|---|---|---|---|---|---|
| Gln | Ile | Pro | Ala | Ala | Val | Gly | Asp | Leu | Pro | Tyr | Leu | Glu | Thr | Leu | Glu | |
| | | | | 85 | | | | | 90 | | | | | 95 | | |

| TTT | CAT | CAT | GTT | ACT | AAT | CTC | ACC | GGA | ACA | ATT | CCA | CCT | GCA | ATT | GCG | 756 |
|---|---|---|---|---|---|---|---|---|---|---|---|---|---|---|---|---|
| Phe | His | His | Val | Thr | Asn | Leu | Thr | Gly | Thr | Ile | Pro | Pro | Ala | Ile | Ala | |
| | | | 100 | | | | | 105 | | | | | 110 | | | |

| AAG | CTC | ACA | AAT | CTC | AAA | ATG | TTA | AGG | CTC | AGC | TTC | ACT | AAC | CTT | ACA | 804 |
|---|---|---|---|---|---|---|---|---|---|---|---|---|---|---|---|---|
| Lys | Leu | Thr | Asn | Leu | Lys | Met | Leu | Arg | Leu | Ser | Phe | Thr | Asn | Leu | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| GGT | CCG | ATC | CCT | GAA | TTC | CTT | AGT | CAG | CTG | AAG | AAT | TTG | ACG | TTG | CTC | 852 |
| Gly | Pro | Ile | Pro | Glu | Phe | Leu | Ser | Gln | Leu | Lys | Asn | Leu | Thr | Leu | Leu | |
| | 130 | | | | 135 | | | | | 140 | | | | | | |
| GAG | TTG | AAT | TAC | AAT | CAA | TTT | ACC | GGA | ACA | ATC | CCT | TCT | TCC | CTC | TCT | 900 |
| Glu | Leu | Asn | Tyr | Asn | Gln | Phe | Thr | Gly | Thr | Ile | Pro | Ser | Ser | Leu | Ser | |
| 145 | | | | | 150 | | | | | 155 | | | | | 160 | |
| CAG | CTT | CCG | AAT | TTG | CTA | GCG | ATG | TAC | TTA | GAT | CGT | AAC | AAA | CTC | ACC | 948 |
| Gln | Leu | Pro | Asn | Leu | Leu | Ala | Met | Tyr | Leu | Asp | Arg | Asn | Lys | Leu | Thr | |
| | | | | 165 | | | | | 170 | | | | | 175 | | |
| GGA | ACA | ATA | CCG | GAA | TCG | TTT | GGG | AGA | TTT | AAA | GGA | CCA | AAT | ATA | CCA | 996 |
| Gly | Thr | Ile | Pro | Glu | Ser | Phe | Gly | Arg | Phe | Lys | Gly | Pro | Asn | Ile | Pro | |
| | | | 180 | | | | | 185 | | | | | 190 | | | |
| GAT | CTC | TAC | CTT | TCA | CAC | AAC | AGC | TTG | ACC | GGA | CAT | GTG | CCG | GCA | TCT | 1044 |
| Asp | Leu | Tyr | Leu | Ser | His | Asn | Ser | Leu | Thr | Gly | His | Val | Pro | Ala | Ser | |
| | | 195 | | | | | 200 | | | | | 205 | | | | |
| TTA | GGT | GAT | TTG | AAT | TTT | TCC | ACG | CTT | GAT | TTC | TCC | AGG | AAT | AAG | CTT | 1092 |
| Leu | Gly | Asp | Leu | Asn | Phe | Ser | Thr | Leu | Asp | Phe | Ser | Arg | Asn | Lys | Leu | |
| | 210 | | | | | 215 | | | | | 220 | | | | | |
| GAA | GGA | GAT | GTT | TCG | TTT | TTG | TTC | GGG | AAG | AAT | AAG | ACG | AGT | CAG | GTA | 1140 |
| Glu | Gly | Asp | Val | Ser | Phe | Leu | Phe | Gly | Lys | Asn | Lys | Thr | Ser | Gln | Val | |
| 225 | | | | | 230 | | | | | 235 | | | | | 240 | |
| ATT | GAT | TTA | TCG | AGG | AAT | TTA | TTG | GAG | TTT | GAT | ATT | TCG | AAA | TCG | GAG | 1188 |
| Ile | Asp | Leu | Ser | Arg | Asn | Leu | Leu | Glu | Phe | Asp | Ile | Ser | Lys | Ser | Glu | |
| | | | | 245 | | | | | 250 | | | | | 255 | | |
| TTT | GCT | GAG | AGC | TTG | ATA | TCA | TTG | GAT | TTG | AAT | CAT | AAT | CGA | ATT | TTT | 1236 |
| Phe | Ala | Glu | Ser | Leu | Ile | Ser | Leu | Asp | Leu | Asn | His | Asn | Arg | Ile | Phe | |
| | | | 260 | | | | | 265 | | | | | 270 | | | |
| GGT | AGC | TTA | CCA | CCA | GGA | TTG | AAA | GAT | GTA | CCA | TTG | CAG | TTT | TTC | AAT | 1284 |
| Gly | Ser | Leu | Pro | Pro | Gly | Leu | Lys | Asp | Val | Pro | Leu | Gln | Phe | Phe | Asn | |
| | | 275 | | | | | 280 | | | | | 285 | | | | |
| GTG | AGT | TAT | AAT | AGA | CTT | TGT | GGA | CAG | ATT | CCA | CAA | GGT | GGA | ACG | TTG | 1332 |
| Val | Ser | Tyr | Asn | Arg | Leu | Cys | Gly | Gln | Ile | Pro | Gln | Gly | Gly | Thr | Leu | |
| | 290 | | | | | 295 | | | | | 300 | | | | | |
| CAG | AGC | TTT | GAT | ATT | TAC | TCT | TAT | TTG | CAT | AAC | AAA | TGC | CTT | TGT | GGC | 1380 |
| Gln | Ser | Phe | Asp | Ile | Tyr | Ser | Tyr | Leu | His | Asn | Lys | Cys | Leu | Cys | Gly | |
| 305 | | | | | 310 | | | | | 315 | | | | | 320 | |
| TCT | CCC | TTG | CCG | AAA | TGT | AAG | TAGGTATGGG | | GGTCGAGGAT | | TTAAATAATC | | | | | 1431 |
| Ser | Pro | Leu | Pro | Lys | Cys | Lys | | | | | | | | | | |
| | | | | 325 | | | | | | | | | | | | |

| | | | | |
|---|---|---|---|---|
| GAGAATTGTA | GTAGAGGCAA | CTAGCCTTCT | CTAGTCGTTC | CTAATCATAT | TTAGTGCTCT | 1491 |
| TTTGGCTTTT | TATAATTCGT | ATGCGAGGGT | CTAATGAATA | TAGTCTCTCT | ATCAATAAAC | 1551 |
| TGGCATCTTC | AGATTCCAGT | TATGAAATTT | TACGAAGTAT | GTTGTTGATC | AATATTACTG | 1611 |
| CCCTTGATTC | ATGTCTTCAT | CTTTTTTTTT | TCTTTTCTCA | AGTTGCAATA | TTTGAAAGCA | 1671 |
| AATTGAATTG | GGCATGTAGT | TACAAACTTT | GAAGTTAGTT | AGTCAATTTG | AATCTTGCAA | 1731 |
| TAGTCAAATG | AGCTAAAGTC | AAAAGTGTAT | TAAAAAATTT | ATAAACAAG | TGCATATAAA | 1791 |
| CAGAGTTGAA | CCAAAGGCTA | ATAGATGGTG | CAAATTGAGG | TGCATTTCAT | TATGGTCGTG | 1851 |
| TTTTTTGTTT | TCATTGGAGG | AGTTCACAAC | GCAAAGTCCG | TGCTAAAGTT | ACTGAATTTT | 1911 |
| TCAATAGAAG | TACAGAATCT | GTGCTAAAAT | TATTTACAGA | ATCTGTGCTA | AAATTATTGA | 1971 |
| GTCATACACT | GTGGAACAGT | TGCAAGATTA | GATGAAGGAA | TTGGTTACTT | CATTGAGAAA | 2031 |
| TTATTTTCAC | AACTTACATT | AATCTTTATC | GATGTTAATA | AACT | | 2075 |

( 2 ) INFORMATION FOR SEQ ID NO:4:

( i ) SEQUENCE CHARACTERISTICS:
        ( A ) LENGTH: 327 amino acids
        ( B ) TYPE: amino acid (D) TOPOLOGY: linear (ii) MOLECULE TYPE: protein (xi) SEQUENCE DESCRIPTION: SEQ ID NO:4:

| Met | Asn | Leu | Ser | Leu | Leu | Leu | Val | Val | Ile | Phe | Leu | Cys | Phe | Ala | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Ser | Leu | Ser | Val | Arg | Cys | Asn | Pro | Lys | Asp | Lys | Lys | Val | Leu | Leu |
|     |     |     | 20  |     |     |     |     | 25  |     |     |     |     | 30  |     |     |

| Gln | Ile | Lys | Lys | Asp | Leu | Gly | Asn | Pro | Tyr | His | Leu | Ala | Ser | Trp | Asp |
|     |     | 35  |     |     |     |     | 40  |     |     |     |     | 45  |     |     |     |

| Pro | Asn | Thr | Asp | Cys | Cys | Tyr | Trp | Tyr | Val | Ile | Lys | Cys | Asp | Arg | Lys |
|     | 50  |     |     |     |     | 55  |     |     |     |     | 60  |     |     |     |     |

| Thr | Asn | Arg | Ile | Asn | Ala | Leu | Thr | Val | Phe | Gln | Ala | Asn | Ile | Ser | Gly |
| 65  |     |     |     |     | 70  |     |     |     |     | 75  |     |     |     |     | 80  |

| Gln | Ile | Pro | Ala | Ala | Val | Gly | Asp | Leu | Pro | Tyr | Leu | Glu | Thr | Leu | Glu |
|     |     |     |     | 85  |     |     |     |     | 90  |     |     |     |     | 95  |     |

| Phe | His | His | Val | Thr | Asn | Leu | Thr | Gly | Thr | Ile | Pro | Pro | Ala | Ile | Ala |
|     |     |     | 100 |     |     |     |     | 105 |     |     |     |     | 110 |     |     |

| Lys | Leu | Thr | Asn | Leu | Lys | Met | Leu | Arg | Leu | Ser | Phe | Thr | Asn | Leu | Thr |
|     |     | 115 |     |     |     |     | 120 |     |     |     |     | 125 |     |     |     |

| Gly | Pro | Ile | Pro | Glu | Phe | Leu | Ser | Gln | Leu | Lys | Asn | Leu | Thr | Leu | Leu |
|     | 130 |     |     |     |     | 135 |     |     |     |     | 140 |     |     |     |     |

| Glu | Leu | Asn | Tyr | Asn | Gln | Phe | Thr | Gly | Thr | Ile | Pro | Ser | Ser | Leu | Ser |
| 145 |     |     |     |     | 150 |     |     |     |     | 155 |     |     |     |     | 160 |

| Gln | Leu | Pro | Asn | Leu | Leu | Ala | Met | Tyr | Leu | Asp | Arg | Asn | Lys | Leu | Thr |
|     |     |     |     | 165 |     |     |     |     | 170 |     |     |     |     | 175 |     |

| Gly | Thr | Ile | Pro | Glu | Ser | Phe | Gly | Arg | Phe | Lys | Gly | Pro | Asn | Ile | Pro |
|     |     |     | 180 |     |     |     |     | 185 |     |     |     |     | 190 |     |     |

| Asp | Leu | Tyr | Leu | Ser | His | Asn | Ser | Leu | Thr | Gly | His | Val | Pro | Ala | Ser |
|     |     | 195 |     |     |     |     | 200 |     |     |     |     | 205 |     |     |     |

| Leu | Gly | Asp | Leu | Asn | Phe | Ser | Thr | Leu | Asp | Phe | Ser | Arg | Asn | Lys | Leu |
|     | 210 |     |     |     |     | 215 |     |     |     |     | 220 |     |     |     |     |

| Glu | Gly | Asp | Val | Ser | Phe | Leu | Phe | Gly | Lys | Asn | Lys | Thr | Ser | Gln | Val |
| 225 |     |     |     |     | 230 |     |     |     |     | 235 |     |     |     |     | 240 |

| Ile | Asp | Leu | Ser | Arg | Asn | Leu | Leu | Glu | Phe | Asp | Ile | Ser | Lys | Ser | Glu |
|     |     |     |     | 245 |     |     |     |     | 250 |     |     |     |     | 255 |     |

| Phe | Ala | Glu | Ser | Leu | Ile | Ser | Leu | Asp | Leu | Asn | His | Asn | Arg | Ile | Phe |
|     |     |     | 260 |     |     |     |     | 265 |     |     |     |     | 270 |     |     |

| Gly | Ser | Leu | Pro | Pro | Gly | Leu | Lys | Asp | Val | Pro | Leu | Gln | Phe | Phe | Asn |
|     |     | 275 |     |     |     |     | 280 |     |     |     |     | 285 |     |     |     |

| Val | Ser | Tyr | Asn | Arg | Leu | Cys | Gly | Gln | Ile | Pro | Gln | Gly | Gly | Thr | Leu |
|     | 290 |     |     |     |     | 295 |     |     |     |     | 300 |     |     |     |     |

| Gln | Ser | Phe | Asp | Ile | Tyr | Ser | Tyr | Leu | His | Asn | Lys | Cys | Leu | Cys | Gly |
| 305 |     |     |     |     | 310 |     |     |     |     | 315 |     |     |     |     | 320 |

| Ser | Pro | Leu | Pro | Lys | Cys | Lys |
|     |     |     |     | 325 |     |     |

(2) INFORMATION FOR SEQ ID NO:5:

(i) SEQUENCE CHARACTERISTICS:
(A) LENGTH: 215 base pairs
(B) TYPE: nucleic acid
(C) STRANDEDNESS: single
(D) TOPOLOGY: unknown (ii) MOLECULE TYPE: protein ( i x ) FEATURE:
  ( A ) NAME/KEY: misc_feature
  ( B ) LOCATION: 1..215
  ( D ) OTHER INFORMATION: /standard_name="Deduced amino acid sequence of PGIP from bean."

( x i ) SEQUENCE DESCRIPTION: SEQ ID NO:5:

| | | | | | |
|---|---|---|---|---|---|
| MTNVTMSSSS | VVSRTASCND | KAKKDGNTTS | SWTTDCCNRT | WGVCDTDTTY | RVNNDSGHNK | 60 |
| YSSANYNYGG | NNVGAAKTHY | YTHTNVSGAD | SKTVTDSYNA | SGTSSSNGGT | DGNRSGADSY | 120 |
| GSSKTAMTSR | NRTGKTANNA | VDSRNMGDAS | VGSDKNTKKH | AKNSADGKVG | SKNNGDRNNR | 180 |
| YGTGTKSNVS | NNCGGGNKRD | VSSYANNKCC | GSSCT | | | 215 |

( 2 ) INFORMATION FOR SEQ ID NO:6:

( i ) SEQUENCE CHARACTERISTICS:
    ( A ) LENGTH: 25 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:6:

Asp Leu Xaa Asn Pro Asp Asp Lys Lys Val Leu Leu Gln Ile Lys Lys
 1               5                  10                 15
Ala Phe Gly Asp Pro Tyr Val Leu Ala
            20              25

( 2 ) INFORMATION FOR SEQ ID NO:7:

( i ) SEQUENCE CHARACTERISTICS:
    ( A ) LENGTH: 31 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:7:

Asp Phe Thr Ser Ile Asp Leu Ser Arg Asn Lys Leu Glu Gly Asp Ala
 1               5                  10                 15
Xaa Val Ile Phe Gly Leu Xaa Lys Thr Thr Gln Ile Val Asp Leu
            20              25              30

( 2 ) INFORMATION FOR SEQ ID NO:8:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:8:

GGAATTCAAY CCNGAYGAYA ARAARGT    27

( 2 ) INFORMATION FOR SEQ ID NO:9:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:9:

GCTCTAGATC DATNGANGTR AARTCCAT 28

( 2 ) INFORMATION FOR SEQ ID NO:10:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:10:

GGAATTCCAR ATHAARAARG CNTTYGG 27

( 2 ) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:11:

TTGTCGACGG ATCCTTCCCC CCCCCCCCCC CCC 33

( 2 ) INFORMATION FOR SEQ ID NO:12:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:12:

TAGACGAAGA GCGCCGA 17

( 2 ) INFORMATION FOR SEQ ID NO:13:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:13:

GACTCGAGTC GACATCGATT TTTTTTTTT TTTTT 35

( 2 ) INFORMATION FOR SEQ ID NO:14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:14:

AGGACTCAAG TCTCTCAG 18

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:15:

ACATCTCTCA GGCTCTCAAC C 21

( 2 ) INFORMATION FOR SEQ ID NO:16:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:16:

AAATTGCTGG CCAAATCTGC AG 22

( 2 ) INFORMATION FOR SEQ ID NO:17:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:17:

Val Arg Xaa Asn Pro Lys Asp Lys Lys Val Leu Leu Gln Ile Asp Asp
1               5                   10                  15
Ile ( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:18:

Gly Asn Pro Tyr His Ile
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:19:

Ala Ser Xaa Asp Pro Asn
1               5

(2) INFORMATION FOR SEQ ID NO:20:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:20:

```
Asp  Leu  Gly  Asn  Pro  Tyr  His  Leu  Ala  Ser  Xaa  Asp  Pro  Asn  Thr  Asp
 1                    5                              10                       15

Cys  Cys  Tyr
```

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:21:

```
Leu  Thr  Gly  Thr  Ile  Pro  Glu  Ser  Phe  Gly  Arg  Phe  Lys
 1                    5                              10
```

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:22:

CARATHAARA ARGAYTTRGG                      20

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:23:

GGAATTCGAY CCNAAYACNG AYTGYTG             27

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:24:

CCRAANGAYT CNGGDATNG                       19